United States Patent
Walters et al.

(10) Patent No.: US 12,089,828 B2
(45) Date of Patent: Sep. 17, 2024

(54) AORTIC CLOSURE SYSTEM AND RELATED METHODS

(71) Applicant: Teleflex Life Sciences LLC, Wilmington, DE (US)

(72) Inventors: Greg A. Walters, Exton, PA (US); Nathaniel Haim Maor, Chester Springs, PA (US); Joseph Todd Grintz, Glenmoore, PA (US); Donald Richard Arnold, Montrose, PA (US); Francois Jouin, Malvern, PA (US)

(73) Assignee: Teleflex Life Sciences LLC, Wilmington, DE (US)

( * ) Notice: Subject to any disclaimer, the term of this patent is extended or adjusted under 35 U.S.C. 154(b) by 213 days.

(21) Appl. No.: 17/581,116

(22) Filed: Jan. 21, 2022

(65) Prior Publication Data
US 2022/0273276 A1   Sep. 1, 2022

Related U.S. Application Data

(60) Provisional application No. 63/154,120, filed on Feb. 26, 2021.

(51) Int. Cl.
*A61B 17/00* (2006.01)
*A61B 17/04* (2006.01)

(52) U.S. Cl.
CPC ...... *A61B 17/0057* (2013.01); *A61B 17/0469* (2013.01); *A61B 2017/00309* (2013.01); *A61B 2017/00623* (2013.01); *A61B 2017/00663* (2013.01); *A61B 2017/00778* (2013.01); *A61B 2017/0409* (2013.01)

(58) Field of Classification Search
CPC .......... A61B 2017/00623; A61B 2017/00663; A61B 2017/00778
See application file for complete search history.

(56) References Cited

U.S. PATENT DOCUMENTS

| | | | |
|---|---|---|---|
| 8,685,059 B2 | 4/2014 | Walters |
| 8,870,917 B2 | 10/2014 | Walters |
| 9,554,785 B2 | 1/2017 | Walters et al. |
| 9,757,104 B2 | 9/2017 | Walters et al. |
| 9,839,417 B2 | 12/2017 | Walters |
| 10,154,835 B2 | 12/2018 | Walters et al. |
| 10,182,804 B2 | 1/2019 | Walters et al. |
| 10,383,611 B2 | 8/2019 | Walters et al. |
| 10,390,810 B2 | 8/2019 | Walters et al. |
| 10,448,937 B2 | 10/2019 | Walters et al. |
| 10,485,524 B2 | 11/2019 | Walters et al. |
| 10,555,727 B2 | 2/2020 | Walters et al. |
| 10,639,019 B2 | 5/2020 | Walters |
| 10,668,253 B2 | 6/2020 | Jacobs |
| 10,682,128 B2 | 6/2020 | Walters et al. |
| 10,835,225 B2 | 11/2020 | Walters et al. |
| 10,905,414 B2 | 2/2021 | Walters et al. |
| 11,020,224 B2 | 6/2021 | Jacobs |
| 11,123,053 B2 | 9/2021 | Walters et al. |

(Continued)

*Primary Examiner* — Alexander J Orkin
(74) *Attorney, Agent, or Firm* — Dorsey & Whitney LLP

(57) ABSTRACT

An aortic closure device for trans-caval procedures having a deployment assembly having a housing, a release tube, and a delivery tube disposed within the release tube, a tamper disposed within the delivery tube, a sealing element, a suture assembly, and an actuator.

17 Claims, 28 Drawing Sheets

(56) References Cited

U.S. PATENT DOCUMENTS

| | | | |
|---|---|---|---|
| 2006/0265007 A1* | 11/2006 | White | A61B 17/0057 606/232 |
| 2009/0216266 A1* | 8/2009 | Maruyama | A61B 17/0057 606/151 |
| 2014/0180332 A1 | 6/2014 | Walters et al. | |
| 2014/0200611 A1 | 7/2014 | Walters | |
| 2017/0100113 A1 | 4/2017 | Walters et al. | |
| 2019/0015204 A1 | 1/2019 | Jacobs | |
| 2019/0015637 A1 | 1/2019 | Jacobs | |
| 2019/0110781 A1 | 4/2019 | Walters et al. | |
| 2019/0142404 A1 | 5/2019 | Walters et al. | |
| 2019/0142418 A1* | 5/2019 | Walters | A61B 17/0487 606/151 |
| 2019/0336116 A1 | 11/2019 | Walters et al. | |
| 2019/0343497 A1* | 11/2019 | Walters | A61B 17/0057 |
| 2020/0000448 A1 | 1/2020 | Walters et al. | |
| 2020/0146661 A1 | 5/2020 | Walters et al. | |
| 2020/0261068 A1 | 8/2020 | Walters et al. | |
| 2020/0289101 A1 | 9/2020 | Walters | |
| 2021/0045724 A1 | 2/2021 | Walters et al. | |
| 2021/0113204 A1 | 4/2021 | Walters et al. | |
| 2022/0031353 A1 | 2/2022 | Arnold et al. | |

* cited by examiner

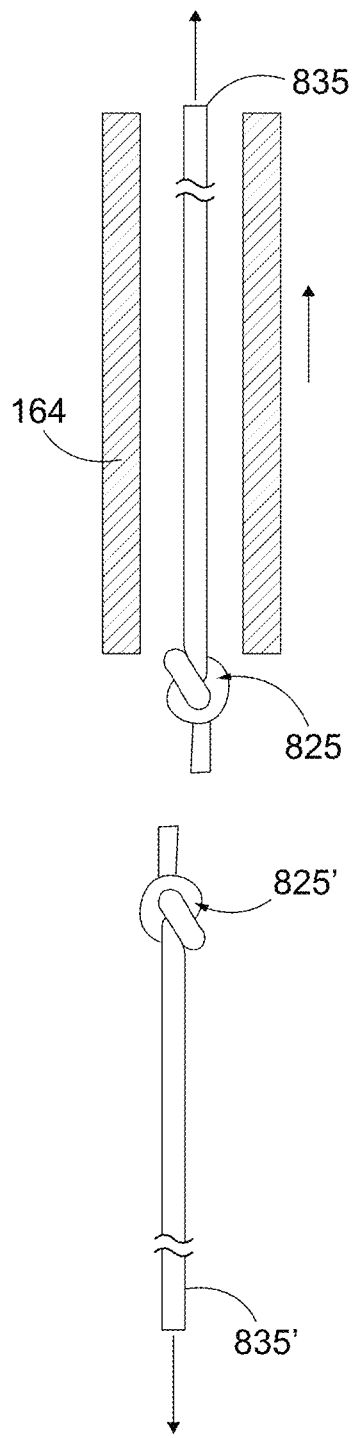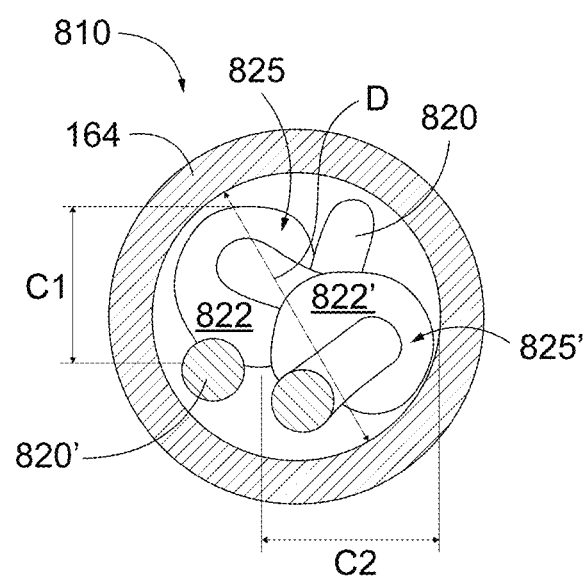
FIG. 8D
FIG. 8E

AORTIC CLOSURE SYSTEM AND RELATED METHODS

CROSS-REFERENCE TO RELATED APPLICATIONS

This application claims the benefit of and priority to, under 35 U.S.C. § 119(e) of U.S. Provisional Application No. 63/154,120 filed on Feb. 26, 2021, the entire contents of which is incorporated herein by reference.

TECHNICAL FIELD

The present disclosure relates to a system and methods for aortic closure and in particular for accessing the aorta through the venous system.

BACKGROUND

Percutaneous procedures often involve accessing vasculature with elongated instruments, e.g., catheters, deployed in an ordered sequence. During an interventional cardiovascular procedure, a puncture may be made in the femoral artery. Advanced cardiovascular procedures may obtain access to the aorta via the vena cava in situations where the femoral artery is not a suitable approach path. In one example, the procedure is a trans-caval aortic valve replacement procedure, or "trans-caval" procedure. Vascular closure devices composed of an absorbable intra-arterial toggle, an extra-vascular folding sealing plug, and a connecting suture, such as a filament, have been developed and may be used to seal these punctures. These devices function by compressing the intra and extra-arterial components together around the puncture, with sufficient tension within the connecting suture. However, these devices are difficult to line up angiographically during the procedure. In addition, as the size of percutaneous sheaths become larger to accommodate larger devices, the size of the resulting puncture increases. Larger punctures are harder to seal because of the larger vessel wall defect or puncture. In the case of sealing blood pressure with an external plug, larger defects expose the plug to increased forces, which must be supported through the connecting suture by the intra-arterial toggle.

SUMMARY

There is a need to provide better aortic closure during surgical procedures. An embodiment of the present disclosure is an aortic closure device. The aortic closure device includes a deployment assembly. The deployment assembly is configured to be inserted in a puncture located in a patient's aorta. The aortic closure device further includes a tamper carried by the deployment assembly, the tamper having a tamper channel that extends therethrough. The aortic closure device further includes a sealing element captured by the deployment assembly. The aortic closure device further includes a suture assembly that extends through the tamper channel such that tamper is movable along the suture assembly, the suture assembly being releasably coupled to the sealing element. The aortic closure device further includes an actuator coupled to the release tube, the delivery tube, and the tamper tube. The actuator has a first actuation phase that causes deployment assembly to release the sealing element therefrom while remaining coupled to the suture assembly. The actuator further has a second actuation phase that causes the tamper to move in the distal direction toward contact with the sealing element. The actuator further has a third actuation phase that causes the tamper to move in a proximal direction that is opposite the distal direction to release the suture assembly from the sealing element.

A further embodiment of the present disclosure is a tamper. The tamper includes a tamper body that is elongate along a longitudinal direction. The tamper body defines a distal end, a proximal end opposite the distal end, and an outer surface. The tamper further includes a tamper channel that extends from the proximal end to the distal end along the longitudinal direction, the tamper channel configured to receive a suture assembly therethrough. The tamper further includes at least one first cut at the distal end and that extends from the outer surface toward the tamper channel. The tamper further includes at least one second cut at the distal end opposite the first cut and that extends from the outer surface toward the tamper channel. The at least one first cut and the least one second cut are configured to permit the distal end of the tamper to flex.

A further embodiment of the present disclosure is a method for sealing a puncture of an artery. The method includes advancing a tamper that extends through at least a portion of a sealing element along a guidewire in a distal direction toward the puncture, the sealing element being coupled to a suture assembly, and, wherein a deployment assembly supports the tamper and releasably holds the sealing element. The method further includes inserting the deployment assembly through the puncture of the artery. The method further includes during a first phase, actuating an actuator of the deployment assembly in a first direction until the deployment assembly releases the sealing element therefrom while remaining coupled to the suture assembly. The method further includes during a second phase, actuating the actuator in a second direction until the tamper moves in the distal direction toward contact with the sealing element. The method further includes during a third phase, actuating the actuator in the first direction until the tamper moves in a proximal direction that is opposite the distal direction and releases the suture assembly from the sealing element.

BRIEF DESCRIPTION OF THE DRAWINGS

The foregoing summary, as well as the following detailed description, will be better understood when read in conjunction with the appended drawings. The drawings show illustrative embodiments of the disclosure. It should be understood, however, that the application is not limited to the precise arrangements and instrumentalities shown.

FIG. 8D is a partial sectional view of the releasable elongated assembly shown in FIG. 8B, illustrating the release member moved to expose the intertwined coupling ends and allows them to release from each other;

FIG. 8E is a cross-sectional view of the releasable elongated assembly taken along line 5-5 in FIG. 2;

DETAILED DESCRIPTION OF ILLUSTRATIVE EMBODIMENTS

Figure 1:
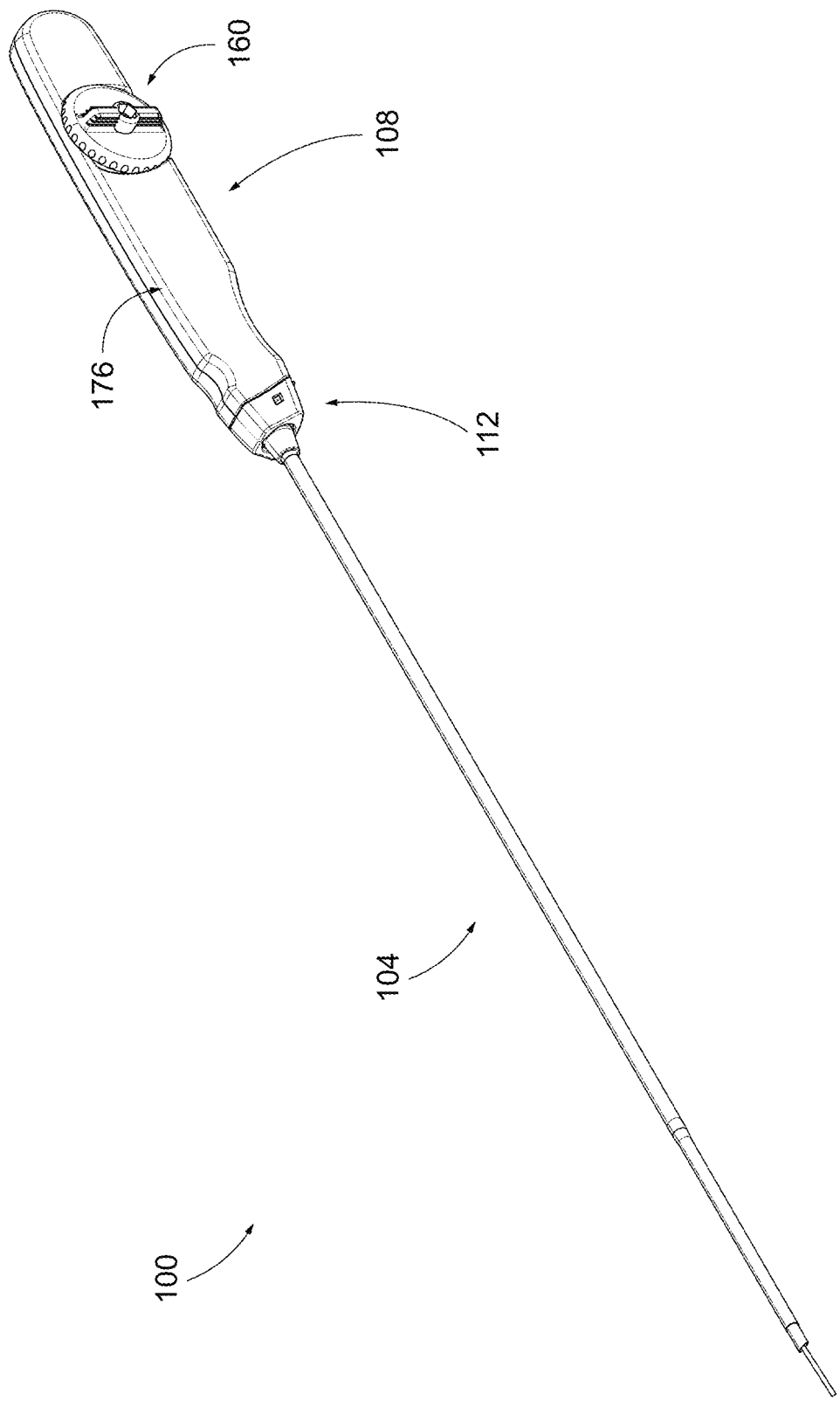
FIG. 1 is a perspective view of an aortic closure system according to an embodiment of the present disclosure.
Figure 2:
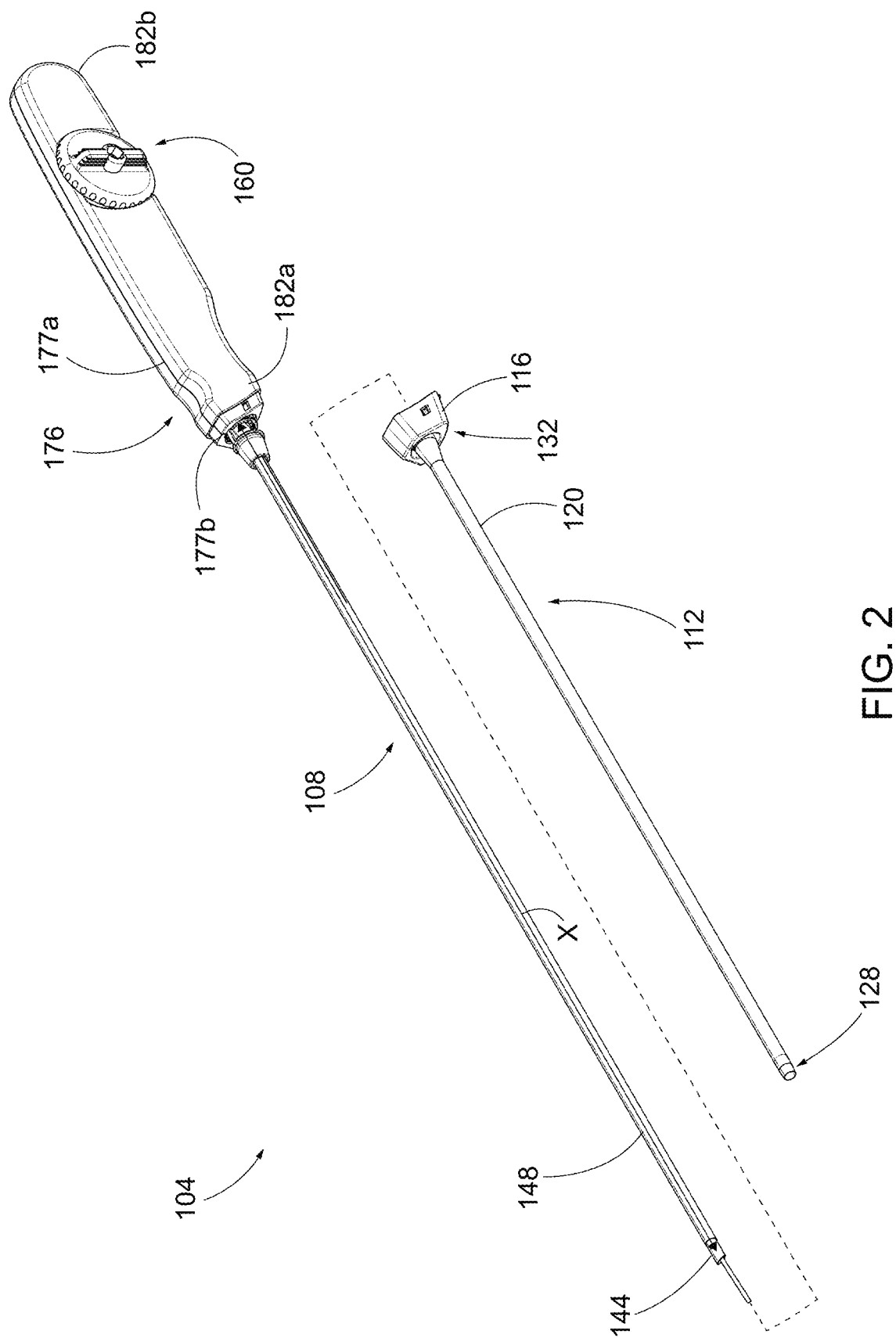
FIG. 2 is a perspective view of the aortic closure device and access sheath of the aortic closure system shown in FIG. 1.

Referring to FIGS. 1-2, the aortic closure system 100 includes a closure device 104 configured to seal the puncture in an aorta or an artery proximate to the aorta. The closure device 104 as described herein may be inserted through a vein, travel through the vein into the vena cava, exit a puncture in the vena cava, and be inserted into a puncture in the aorta to close said puncture. Such closure is performed following a so-called trans-caval procedure. Because of the length between cutaneous access points in vein and puncture locations, the aortic closure system 100 as described herein is configured for remote release of a sealing element, remote tamping of the sealing element, and remote release of a suture from the sealing element. More specifically, sealing element release, tamping, and suture assembly release are controlled via one or more actuators 160 located outside of the patient. In typical closure devices use for closing peripheral femoral arteries or even veins, so-called remote release-tamp-suture release is not required. Thus, the aortic closure systems 100 as described herein are unique and have been developed in view of the unpredictable clinical settings presented by attempt to reliably close a puncture in the aorta through the venous wall.

As shown in FIGS. 1 and 2, the aortic closure system 100 includes an access sheath 112, a deployment assembly 108 configured to be coupled to the access sheath 112, a sealing element 136 (FIG. 3D) carried by the deployment assembly 108, and at least one actuator 160 configured to control release and deployment of the sealing element 136. In addition, the system may include a double length and tapered dilator 908 used to facilitate sheath exchange and insertion of the devices as described herein into the patient.

Figure 3A:
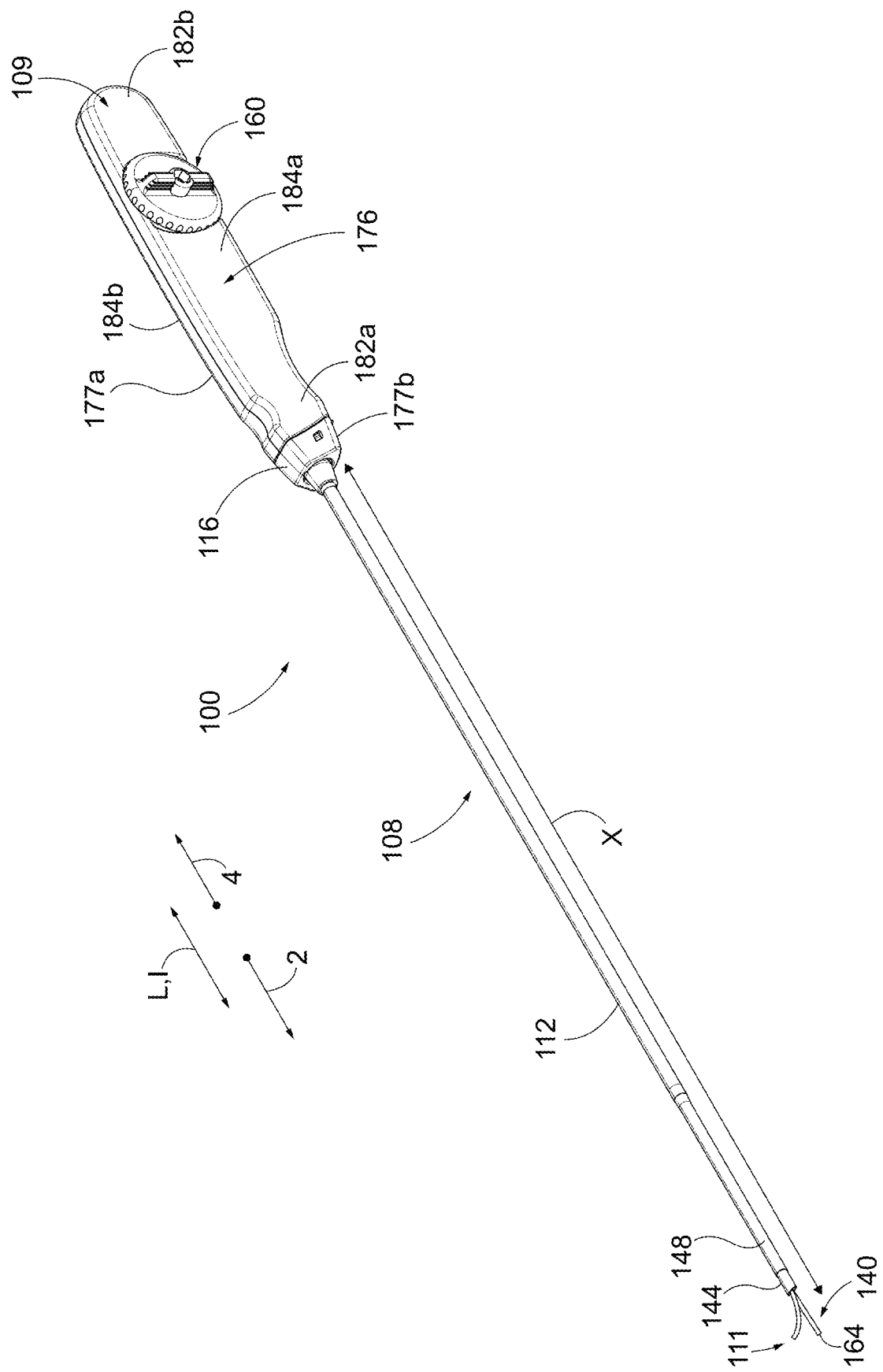
FIG. 3A is a perspective view of an aortic closure device in accordance with an embodiment of the present disclosure.
Figure 3B:
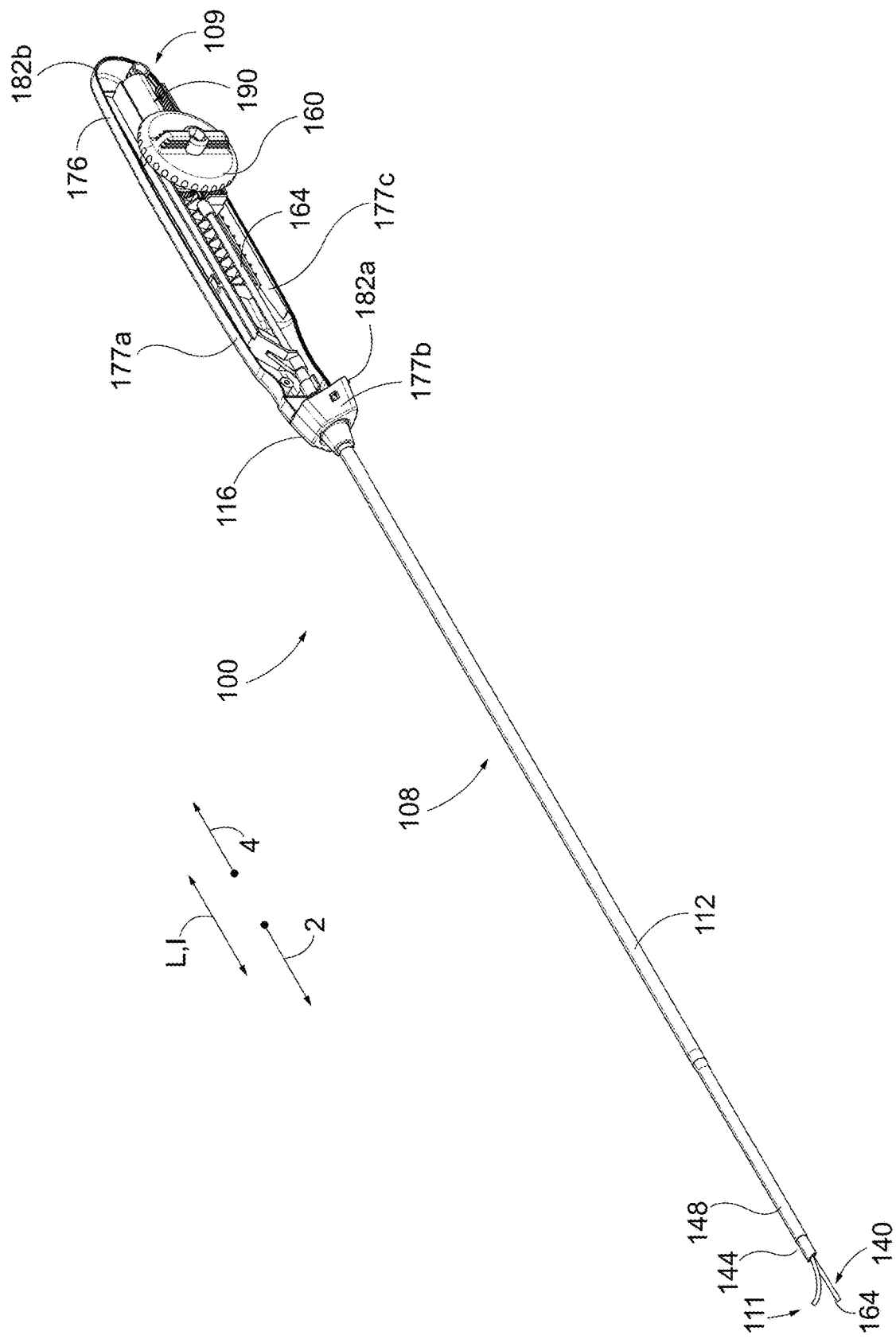
FIG. 3B is a partial cut-away view of the aortic closure device shown in FIG. 3A.

Continuing with FIGS. 2-3B, the access sheath 112 includes a hub 116 and shaft 120 that extends from the hub 116 in the distal direction 2. The access sheath 112 has a front end 128, a rear end 132 opposite to the front end 128, and a lumen (not numbered) that extends from the front end 128 to the rear end 132. The rear end 132 of the access sheath includes the hub 116 that is configured to be coupled to a portion of the deployment assembly 108. When the access sheath 112 is coupled to the deployment assembly 108, the shaft 120 extends in a distal direction. The access sheath 112 can be inserted into position along a dilator 908 that is inserted into the vein. See FIGS. 9C and 9D.

Referring to FIGS. 3A-3D, the deployment assembly 108 is elongate along a longitudinal direction L and includes a rear end 109 and a front end 111 spaced from the rear end 109 along an axis that is aligned with the longitudinal direction L. The longitudinal direction L can include and is aligned with a distal direction 2. The distal direction 2 generally extends from the rear end 109 toward the front end 111, i.e. in a direction away from the user. Further, the longitudinal direction L can be aligned with a proximal direction 4 that is opposite the distal direction 2 and that extends from front end 111 toward the rear end 109 (i.e. toward the user).

Figure 3C:
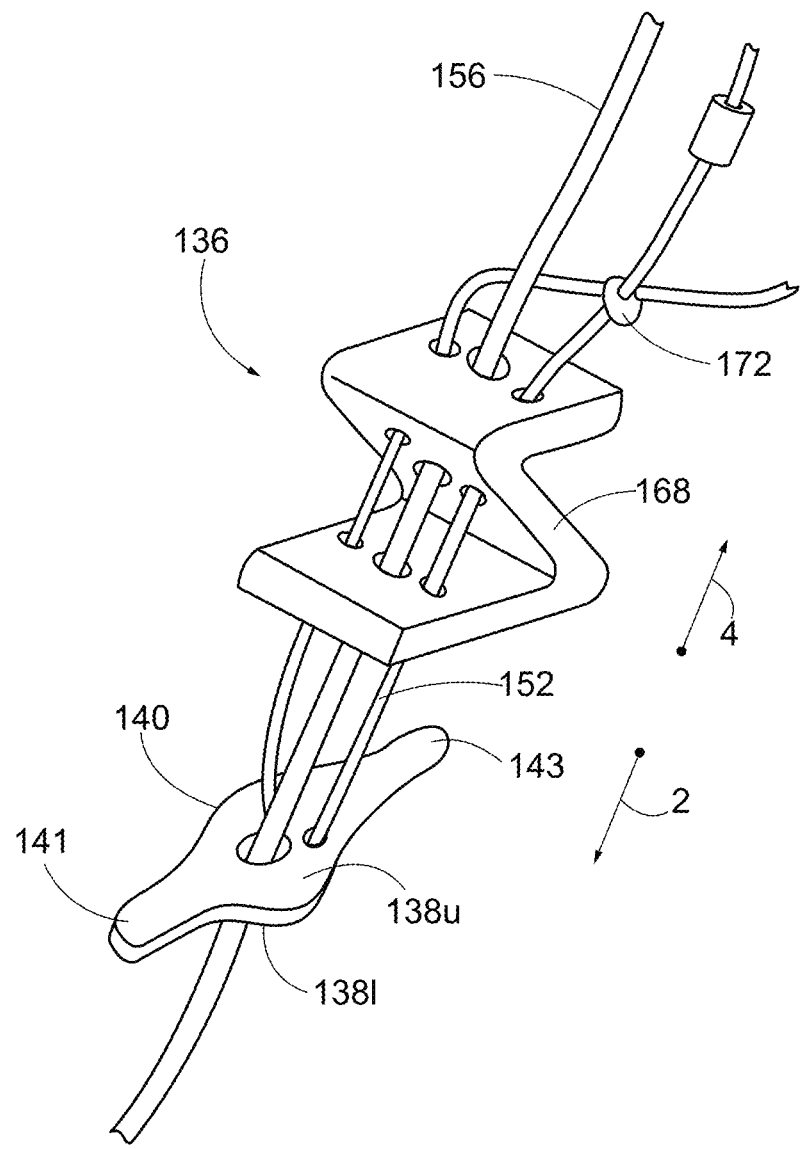
FIG. 3C is a perspective view of a sealing device associated with the aortic closure device shown in FIG. 3A.
Figure 3D:
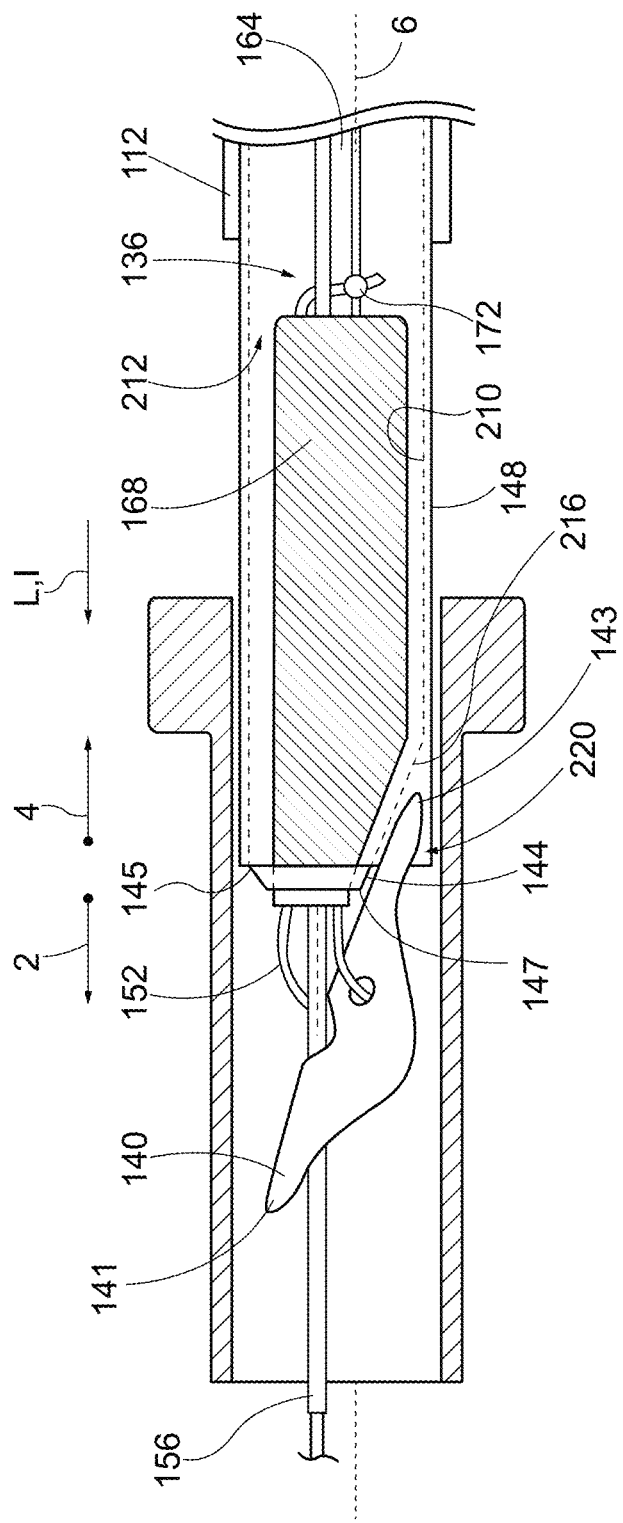
FIG. 3D is a side sectional view of a distal portion of the aortic closure device shown in FIG. 3A.

Turning to FIGS. 3C and 3D, the sealing element 136 may be carried by the deployment assembly 108 and coupled to a suture assembly 152. The sealing element 136 includes the toggle 140 (or anchor) connected to a suture assembly 152, and a plug 168 coupled to the suture assembly 152 and spaced from the toggle 140 in a proximal direction 4. The toggle 140 includes a distal end 141 and a proximal end 143 opposite to the distal end 141, and a plurality of apertures (not numbered) extending therethrough. The toggle 140 has an upper surface 138$u$, a lower surface 138$l$ opposite the upper surface 138$u$, and a thickness (not numbered) that extend from the upper surface 138$u$ to the lower surface 138$l$. The thickness of the toggle 140 may be between about 1 mm and 2 mm. The toggle 140 has a length L that extends from the proximal end 143 to the distal end 141. The length of the toggle 140 is between about 2 cm and 2.5 cm. The toggle 140 further defines a width that extends from and between opposing sides of the toggle 140 along a direction that is perpendicular to the length and the thickness. The width of the toggle 140 at its widest point is between about 6 mm and 8 mm. The apertures extends from the upper surface 138*u* to the lower surface 138*l*. The suture assembly 152 extends through the apertures as illustrated such that an end of the suture assembly 152 is formed into a slidable knot 172. The knot 172 is slidable along the suture assembly 152. In an implanted state, the toggle 140 is adjacent to an inner surface of the aorta and the toggle 140 and the plug 168 are squeezed against the aorta to seal the puncture.

The sealing element 136 is formed with materials suitable for surgical procedures. In the illustrated embodiment, the toggle 140 is made of stainless steel. In other embodiments, the toggle 140 can be made of a polylactic-coglycolic acid or other synthetic absorbable polymer that degrades in the presence of water into naturally occurring metabolites. In further embodiments, the toggle can be made of biocorrodible iron, and biocorrodible magnesium, or other biocompatible materials. It should be appreciated, however, that the toggle 140 can be made of other materials and can have other configurations so long as it can be seated inside the aorta or nearby artery against the arterial wall. The plug 168 can comprise a strip of compressible, resorbable, collagen foam and can be made of a fibrous collagen mix of insoluble and soluble collagen that is cross linked for strength. It should be appreciated, however, that the plug 168 can have any configuration as desired and can be made from any material as desired. The suture assembly 152 can be any elongate member, such as, for example a filament, thread, or braid.

The closure device 104 is configured such that after a distal end of the deployment assembly 108 is inserted through a puncture site of the aorta, the sealing element 136 is deployed to thereby seal or otherwise close the puncture site of the aorta. The deployment assembly 108 is configured to control orientation of a toggle 140 of the sealing element 136 in an easier and more efficient manner during deployment of the sealing element 136. Specifically, the deployment assembly 108 is configured to insert the toggle 140 into the aorta along an insertion direction I. The longitudinal direction L can be aligned with the insertion direction I during a portion of the sealing procedure. Furthermore, the deployment assembly 108 is configured to reduce forces required to deploy the sealing element 136 and seal the puncture.

Continuing with FIGS. 2-3D, the deployment assembly 108 includes a handle member 176, release component 144, a delivery component 148, a tamper 164, the actuator 160, and a tensioner 180. As shown, the release component 144 extends relative to the handle member 176 in the distal direction 2. The delivery component 148 is positioned over or at least partially around the release component 144 and also extends relative to the handle member 176 in the distal direction 2. The tamper 164 is positioned within the release component 144 and is moveable relative to the release component. The suture assembly 152 extends from the sealing element, specifically the toggle 140, through the delivery component 148, through the tensioner 180 around the pulley 200 which is coupled to the housing 177*a* of handle member 176. In one embodiment, the deployment assembly 108 may further include a guide member 156 that receives a guide wire therethrough. The guide member 156 extends through the sealing element 136. In another example, the deployment assembly 108 can be configured so that the guide member 156 extends along the side of the toggle 140.

Referring to FIGS. 2-3B, the handle member 176 includes a housing 177*a* and a cavity 177*c* defined at least partly by housing 177*a* and a nose 177*b* of the access sheath 112. The housing 177*a* is sized to fit in the hand of user and has a forward end 182*a* and rear end 182*b* and opposed sides 184*a* and 184*b*. The actuator is located on one side 184*a*. The cavity 177*c* is sized and configured to carry and support the release component 144, the delivery component 148, the tamper 164, a part of the actuator 160, and the tensioner 180 (not depicted). The release component 144, the delivery component 148, and the tamper 164 extend relative to the handle member 176 in the distal direction 2.

Figure 4A:
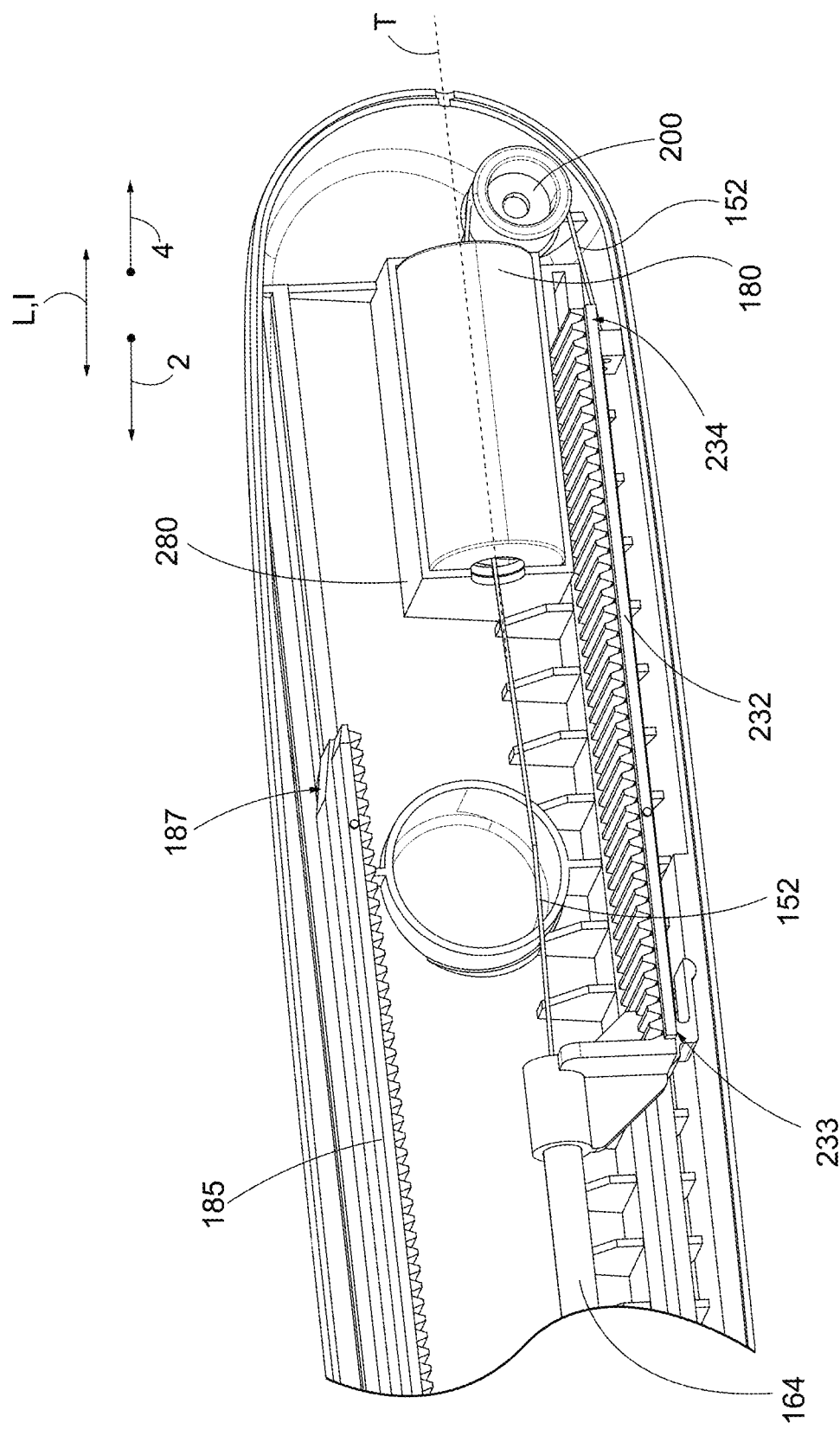
FIG. 4A is a side view of the tensioner and suture of the aortic closure device shown in FIGS. 3A-3B.
Figure 4B:
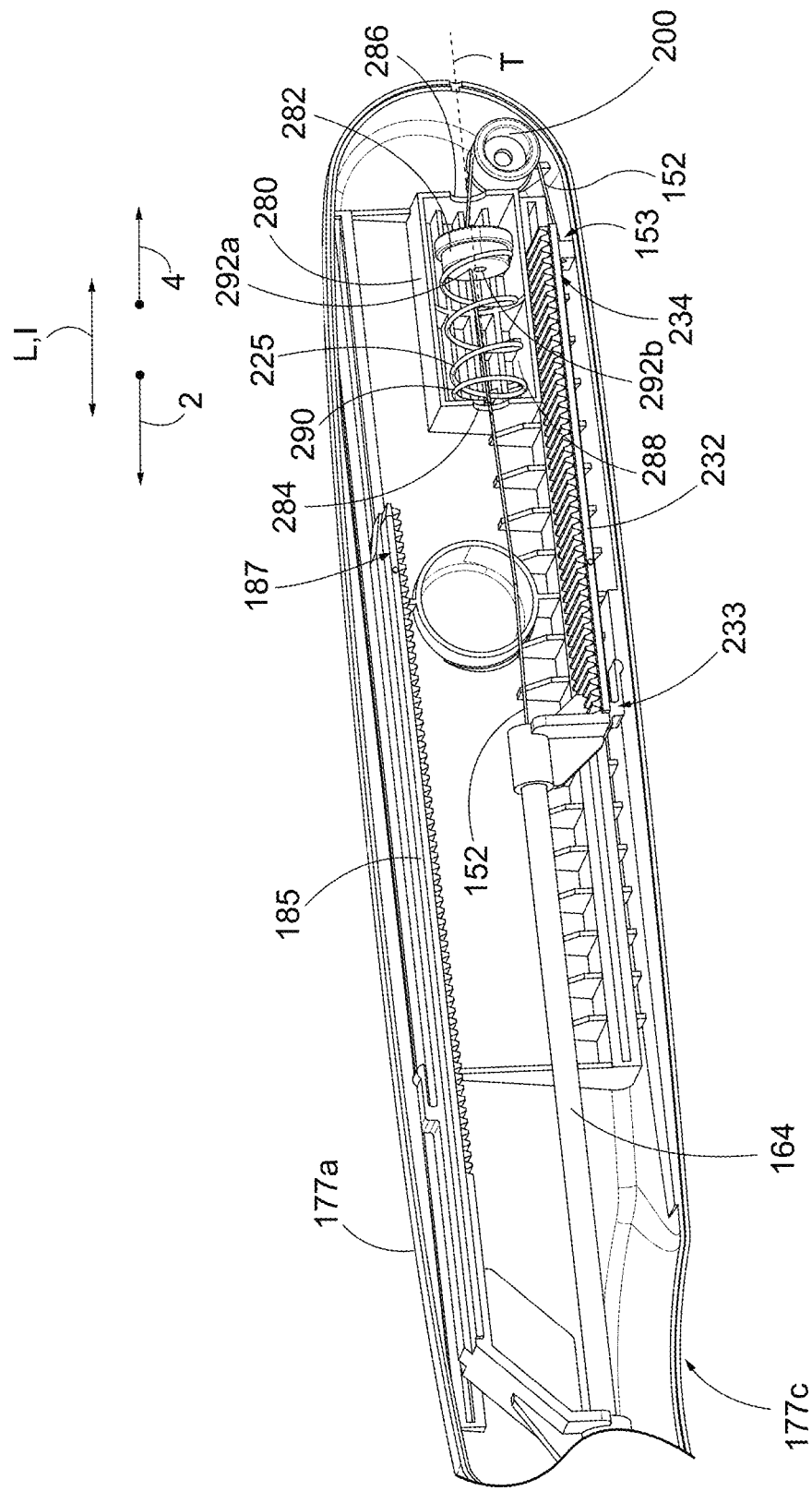
FIG. 4B is a side view of the tensioner and suture of the aortic closure device shown in FIG. 4A, with portions of the device removed for clarity.
Figure 4C:
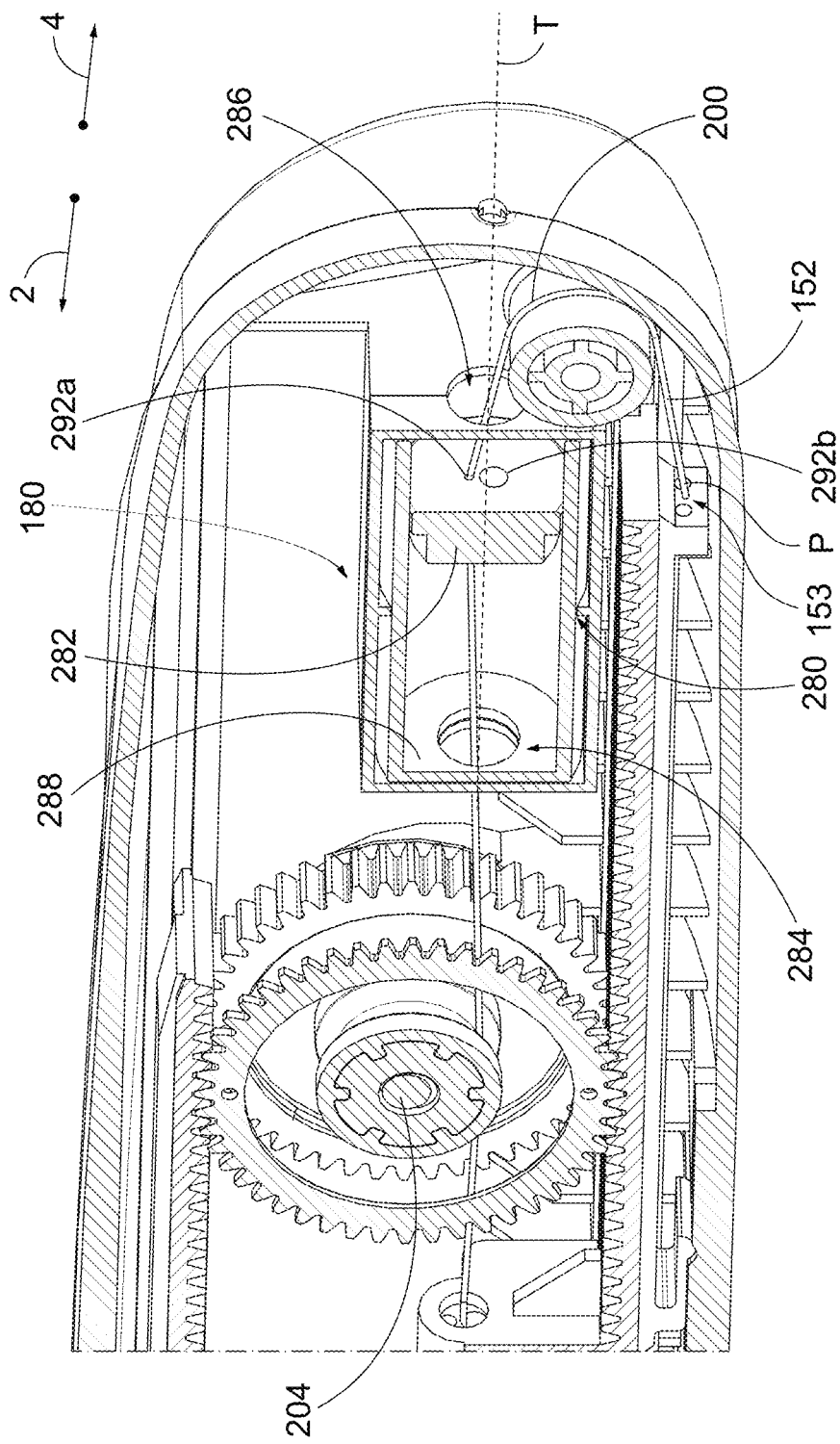
FIG. 4C is a detailed partial section view of the tension shown in FIGS. 4A and 4B.

Referring to FIGS. 4A-4C, the tensioner 180 is disposed proximal to the drive member 204 so as to receive the suture assembly 152 as noted above. In accordance with the illustrated embodiment, the tensioner 180 includes a tensioner housing 280, a drag member 282, and a spring 290 positioned adjacent to the drag member 282. The drag member 282 is moveable within the housing 280. The housing 280 includes a forward aperture 284 and a rearward aperture 286 that is aligned with respect to each other along a tensioner axis T. The housing 280 defines an inner surface 288, which defines an internal space where the spring 290 (spring not shown in FIG. 4C) is located. The drag member 282 includes a first hole 292*a* through which the suture assembly 152 extends and a second hole 292*b* through which a guidewire may extend. The second hole 292*b* may be aligned with the forward aperture 284 and the rearward aperture 286 along the axis T. The drag member 282 is movable along the inner surface 288. As shown, the spring 290 is positioned inside the tensioner housing 280 with one end abutting the inner surface 288 proximate the forward aperture 284 and its opposite end abutting the drag member 282. As shown, a terminal end 153 of the suture assembly 152 is coupled to the housing 177*a* at a fixation point P. In one embodiment, the terminal end 153 is tied around a fastener coupled to the housing 177*a*. The fastener may be coupled to an o-ring that is attached to the housing 177*a*. The o-ring may provide tension relief to prevent over-tensioning.

From there, the suture assembly 152 extends around a pulley 200, through the rearward aperture 286 into the tensioner housing 280, through the drag member 282 (via hole 292*a*) and spring 290 and then exits through the forward aperture 284 and into the tamper 164. Here, the drag member 282 applies a frictional force to the suture assembly 152 at the first hole 292*a* when the suture assembly 152 is placed in tension, such as when the tamper 164 is advanced in the distal direction 2 against the sealing element 136. This, in turn, causes the drag member 282 to advance in a distal direction 2 toward the forward aperture 284, compressing the spring 290. The spring force of the spring 290 can be selected to manage tension along the suture assembly 152 during this phase of actuation. A knot that is slightly larger than the first hole 292*a* may be tied on the suture assembly 152 proximal to the drag member 282 to allow the spring 290 to remain in tension and providing tension to the deployment assembly 108.

Figure 5A:
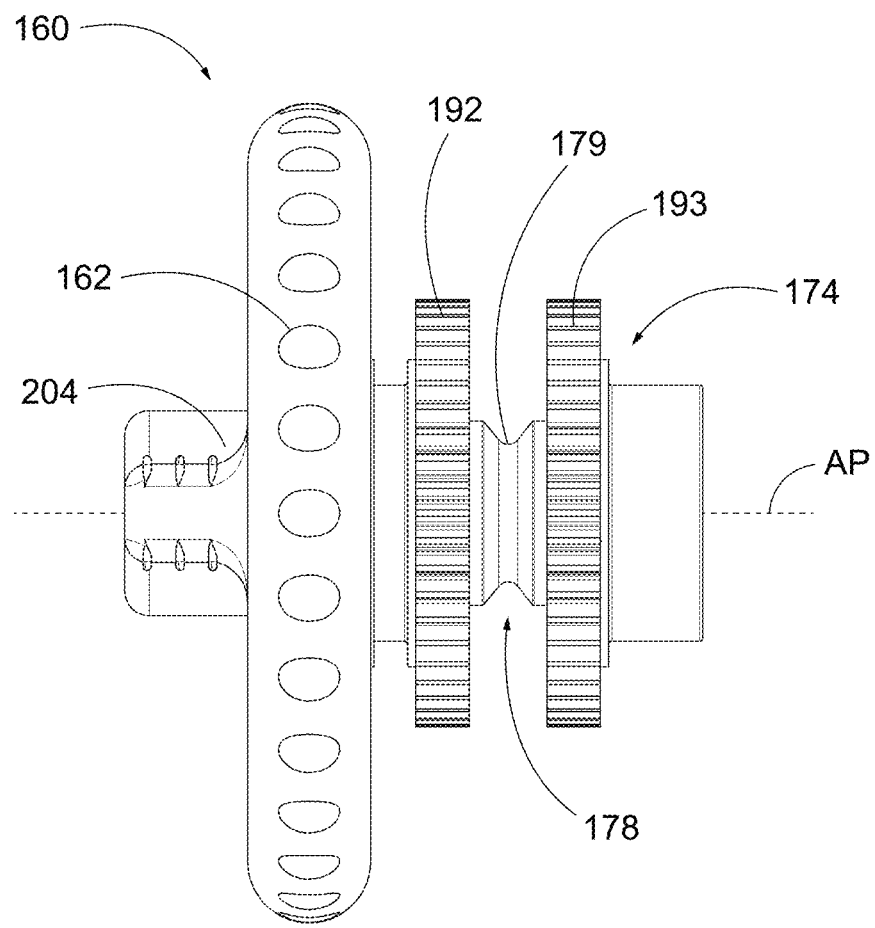
FIG. 5A is an end view of the actuator illustrated in FIGS. 1-3B, according to an embodiment of the present disclosure.
Figure 5B:
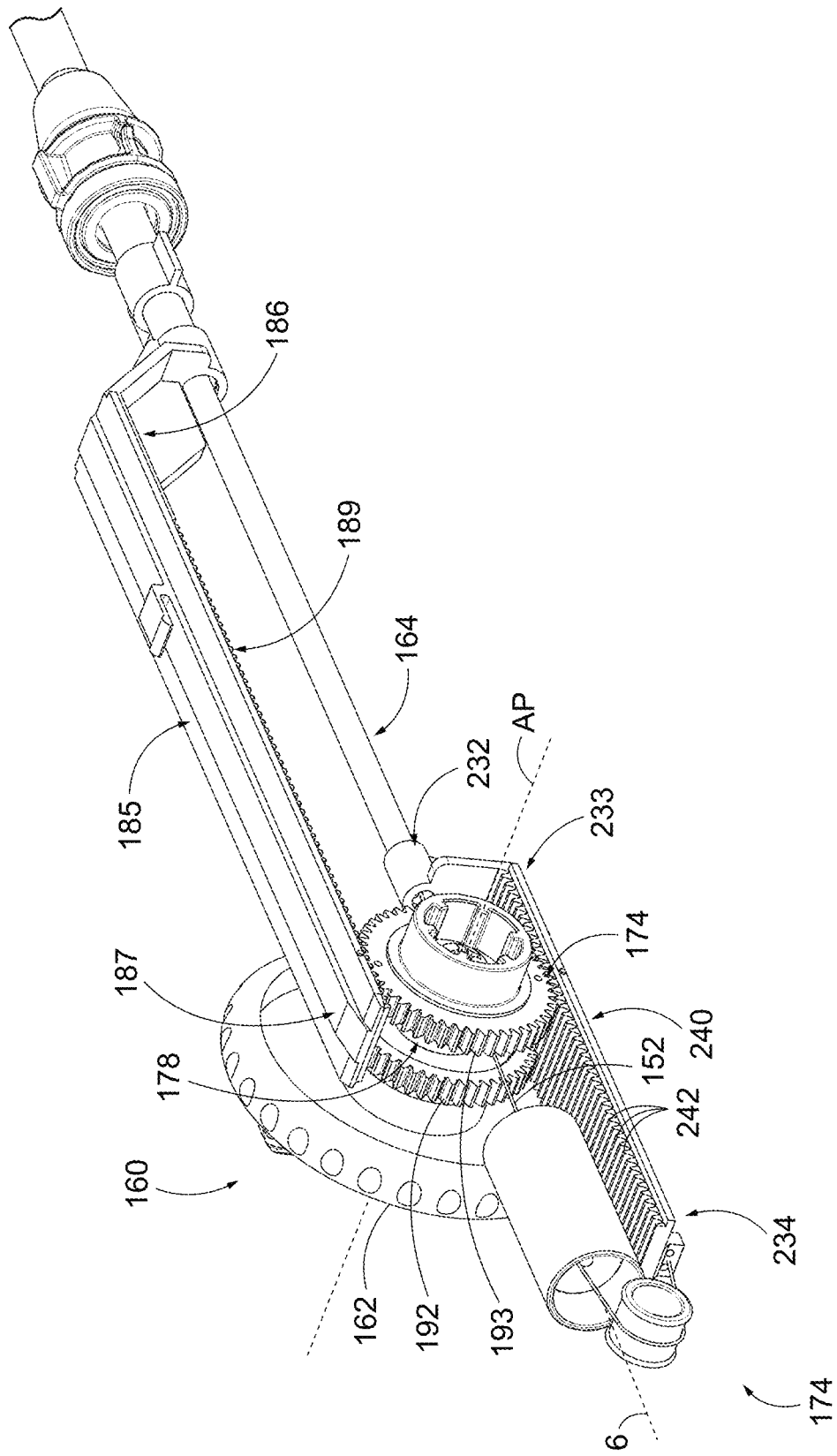
FIG. 5B is an rear perspective view of the actuator, tamper, and release components illustrated in FIG. 3B, with portions of the device removed for clarity.

Referring to FIGS. 5A and 5B, the actuator 160 is configured to release sealing element 136, tamp the sealing element 136, and in some instances, separate the suture assembly 152 from the sealing element 136 once the sealing element 136 is tamped. In accordance with the illustrated embodiment, the actuator 160 may include a knob 162, a drive member 204 fixed to the knob 162, a gear assembly 174 and a suture track 178. The actuator 160, in particular the knob 162 and drive member 204, are rotatable about a rotation axis AP that is perpendicular to the axis 6. The rotation axis AP may or may not intersect axis 6. The gear assembly 174 and suture track 178 are fixed to the drive member 204. In accordance with the example actuator shown, the gear assembly 174 includes a first gear 192 and a second gear 193 separated by the suture track 178. The suture track 178 includes a smooth surface 179 along which the suture assembly 152 extends.

The actuator 160 may be referred to as a two-way actuator. For instance, in use, as the actuator 160 rotates in a first direction about the axis AP, the release component 144 translates along the longitudinal direction L in a proximal direction 4 to release the sealing element. As the actuator 160 rotates in a second direction about the rotation axis AP, the tamper 164 translates along longitudinal direction L in the distal direction 2 toward the sealing element 136. Regardless of which direction the knob is rotated, as a user rotates the knob 162, the drive member 204 rotates, thereby causing the gear assembly 174 to rotate, which causes the actuator 160 to transition through the actuation phases described further below in the present disclosure. It should be appreciated, however, that the actuator 160 can have other configurations as desired and described above, and is not limited to the disclosed knob. For example, the actuator 160 can include a lever. In addition, the knob 162 may be positioned at the distal end of the handle member 176 such that rotation about the axis 6 causes actuation of the actuator 160 and its components. For example, the actuator 160 may be one or more linear sliders. In another embodiment, the actuator 160 may include a rotatable linkage.

Figure 6A:
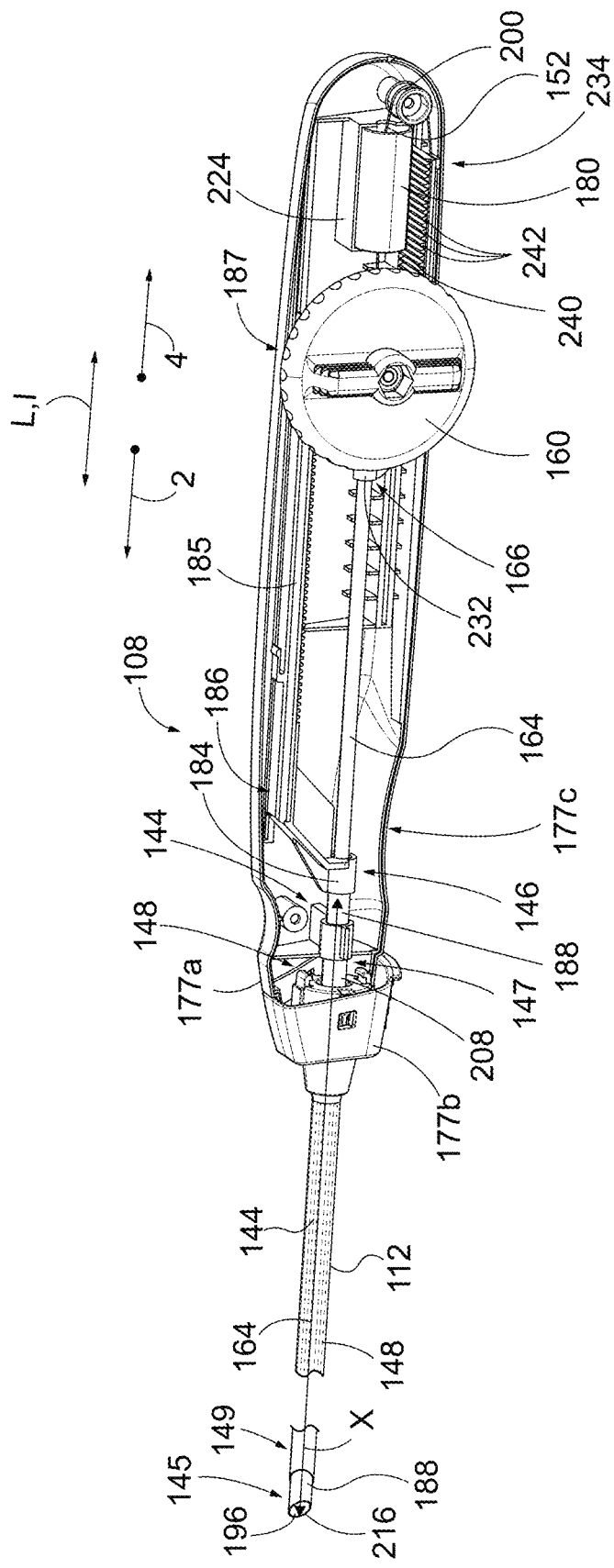
FIG. 6A is a rear perspective view of the aortic closure device shown in FIG. 3B when the actuator is actuated in a first direction, with portions of the device removed for clarity.
Figure 6B:
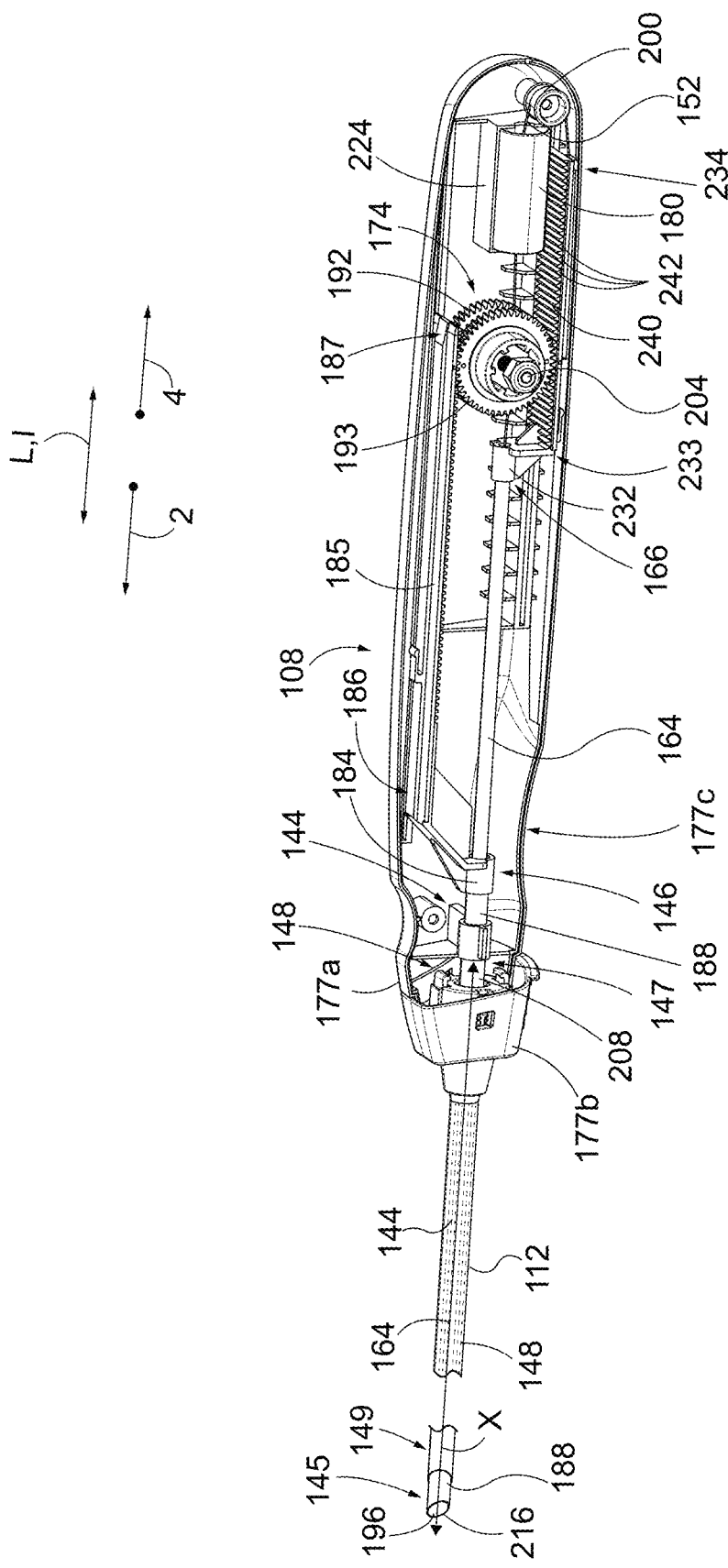
FIG. 6B is a rear perspective view of the aortic closure device shown in FIG. 6A when the actuator is actuated in a first direction, with portions of the device removed for clarity.

Referring to FIGS. 6A and 6B, the release component 144 is elongate along a longitudinal direction L and includes a distal end 145 and a proximal end 146 spaced from the distal end 145 along the longitudinal direction L. In the illustrated embodiment, the release component 144 may extend distally from a distal-most surface a length X of at least approximately 30 cm. In this regard, the length X is parallel to the longitudinal direction L and extends from the distal-most surface of the handle member 176 to the distal end 145 of the release component 144. In other embodiments, the length X of the release component 144 may vary.

In accordance with the illustrated embodiment, the release component 144 includes a release hub 184, a release tube 188 that is fixed to the release hub 184 and extends from the release hub 184 in the distal direction 2, and at least one track 185. The track 185, which may be referred to as the release track 185, has a distal end 186 coupled to the release hub 184, a proximal end 187, and a series of gear teeth 189. The gear teeth 189 are configured to intermesh with the first gear 192 and the second gear 193 of the actuator 160. Thus, the actuator 160 is operably coupled to the release component via engagement of the track 185 with the gear assembly 174 of the actuator 160. In use, the gear assembly 174 transfers motion of the actuator 160 to the release component 144. As a result, actuation of the actuator 160 causes the first gear 192 and the second gear 193 to move the track 185, cause the track 185, and thus the release component 144 to translate along the longitudinal direction L. For instance, in the illustrated embodiment, the rotation of the actuator causes the release component to translate in a proximal direction 4. It should be appreciated, however, that the track 185 can have any configuration as desired.

Figure 6C:
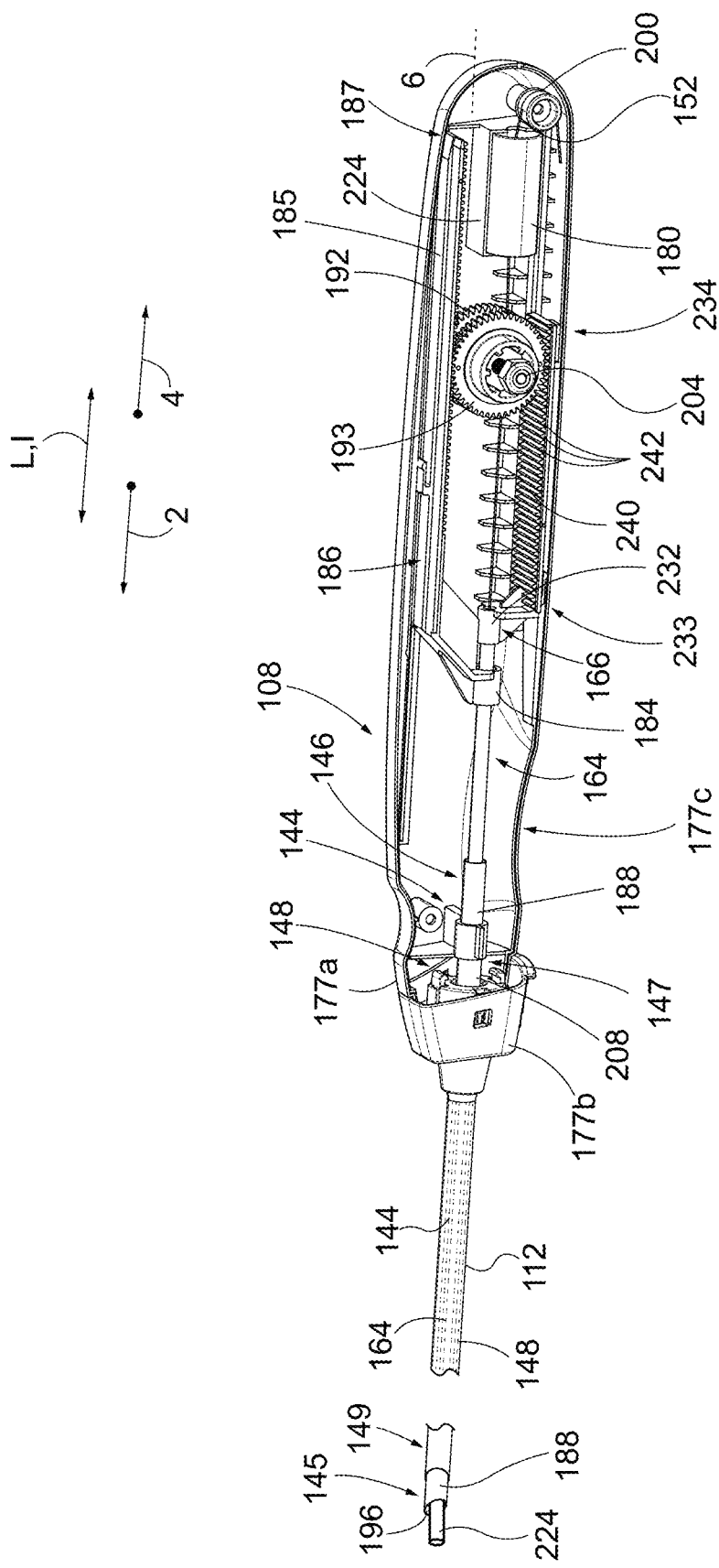
FIG. 6C is a rear perspective view of the aortic closure device shown in FIGS. 6A-6B when the actuator is actuated in a second direction, with portions of the device removed for clarity.

Referring to FIGS. 6A-6C, the release tube 188 is elongate along the longitudinal direction L. The release tube 188 defines a release tube channel 196 that extends along the longitudinal direction L from the hub 184 toward the proximal end 146. In the illustrated embodiment, the release tube channel 196 extends completely through the release tube 188 from the hub 184 to the distal end 145. Furthermore, in the illustrated embodiment the release tube 188 is cylindrical such that the release tube channel 196 is radially enclosed. It should be appreciated, however, that the release tube channel 196 can extend partially through the release tube 188 as desired and that the release tube 188 can have other configurations as desired. For example, the release tube 188 can be U-shaped such that the release tube channel 196 is partially radially open. As shown, the release tube channel 196 is sized to slidably receive the tamper 164 therein. The release component 144 is also movable relative to the delivery component 148 along the longitudinal direction L.

Continuing with FIGS. 6A-6C, the delivery component 148 extends along and around the release component 144 toward the front end 111 of the deployment assembly 108. The delivery component 148 includes a delivery tube body 208 that is elongate along the longitudinal direction L and includes a proximal end 147 and a distal end 149 spaced from the proximal end 147 in the longitudinal direction L. The delivery tube body 208 is fixed to housing 177a at its proximal end 147. In this manner, the release component can translate relative to the delivery component 148. While the description above refers to the release component 144 being moveable relative to the delivery component 148, the deployment assembly 108 can be configured so that the delivery component 148 is moveable relative to the release component 144.

Continuing with FIGS. 6A-6C, the delivery tube body 208 defines a delivery tube channel (not depicted) that extends at least partially through the delivery tube body 208 along the longitudinal direction L. In the illustrated embodiment, the delivery tube channel extends completely through the delivery tube body 208 from the distal end 149 to the proximal end 147. Furthermore, in the illustrated embodiment the delivery tube body 208 is cylindrical such that the delivery tube channel is radially enclosed. It should be appreciated, however, that the delivery tube body 208 can have other configurations as desired. For example, the delivery tube body 208 can be U-shaped such that the delivery tube channel is partially radially open. As illustrated, the proximal end 147 of the delivery component 148 is configured to hold at least a portion of the sealing element 136 (FIG. 3D) while the release component is configured to slide along the delivery component 148.

As shown in FIGS. 3D and 6A-6C, the delivery tube body 208 is sized to retain at least a portion of the sealing element 136. The plug 168 and locking member 230 are retained within the delivery tube body 208, while the toggle 140 is configured to be initially trapped between the delivery component 148 and a distal end of the release component 144. For instance, the distal end 145 of the release tube 188 defines an offset surface 216, which is angled with respect to the longitudinal axis 6. The offset surface 216 and inner surface 210 of the delivery tube body 208 define a cavity that receives the proximal end 143 of the toggle 140 when release component 144 is in the initial configuration. The angle of the offset surface 216 can define the orientation of the toggle 140 in this initial position, whereby the distal end 141 of the toggle 140 is spaced some distance in the distal direction 2 beyond the distal ends 145 and 147 of the release component 144 and delivery component 148, respectively.

Referring to FIGS. 7A-7D, the tamper 164 is configured to tamp the lock and plug in place to aid in sealing the puncture. As illustrated, the tamper 164 includes a tamper tube body 224 that is elongate along the longitudinal direction L and defines a distal end 165, a proximal end 166 (FIGS. 5A-5C) spaced from the distal end 165 in the longitudinal direction L, and an outer surface 167. In the illustrated embodiment, the tamper 164 has a length of about 60 cm. The tamper tube body 224 may have a length of approximately 30 cm. In other embodiments, the length of the tamper tube body 224 may vary. The tamper tube body 224 defines inner surfaces 222, which in turns defines a first tamper channel 226 and a second tamper channel 227. The first tamper channel 226 and the second tamper channel 227 each extend through the tamper tube body 208 from the proximal end 166 to the distal end 165 along the longitudinal direction L. As shown, the first tamper tube channel 226 is larger in diameter than the second tamper tube channel 227. The first tamper tube channel 226 is configured to allow the guidewire (or guide member 156) to pass through it. The second tamper tube channel 227 is configured to allow the suture assembly 152 to pass through the channel 227, including a splice 810 shown and described below. As shown, the tamper tube body 224 is cylindrical such that the first and second tamper tube channels 226, 227 are radially enclosed.

Figure 7A:
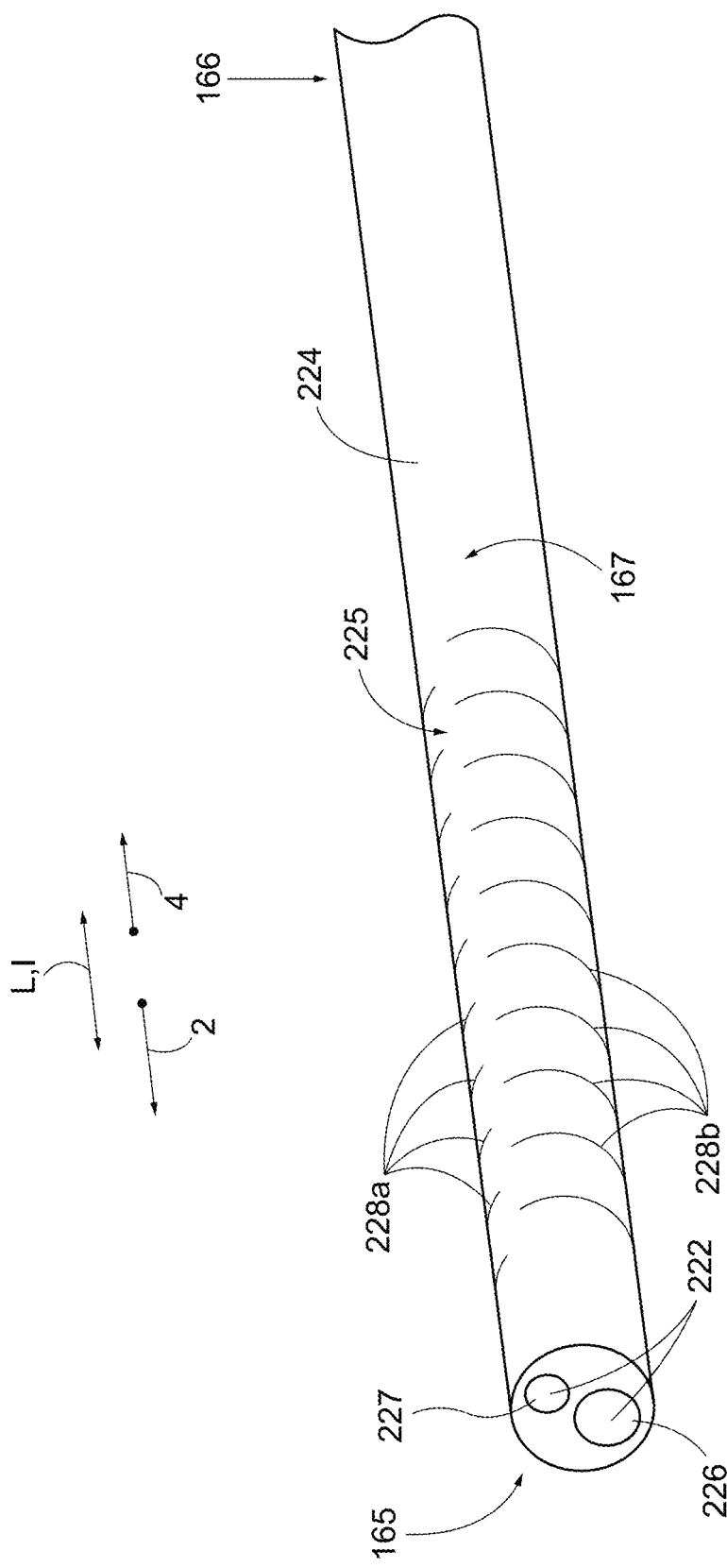
FIG. 7A is a perspective view of a distal portion of a tamper of the aortic closure device shown in FIGS. 3A-3B.
Figure 7B:
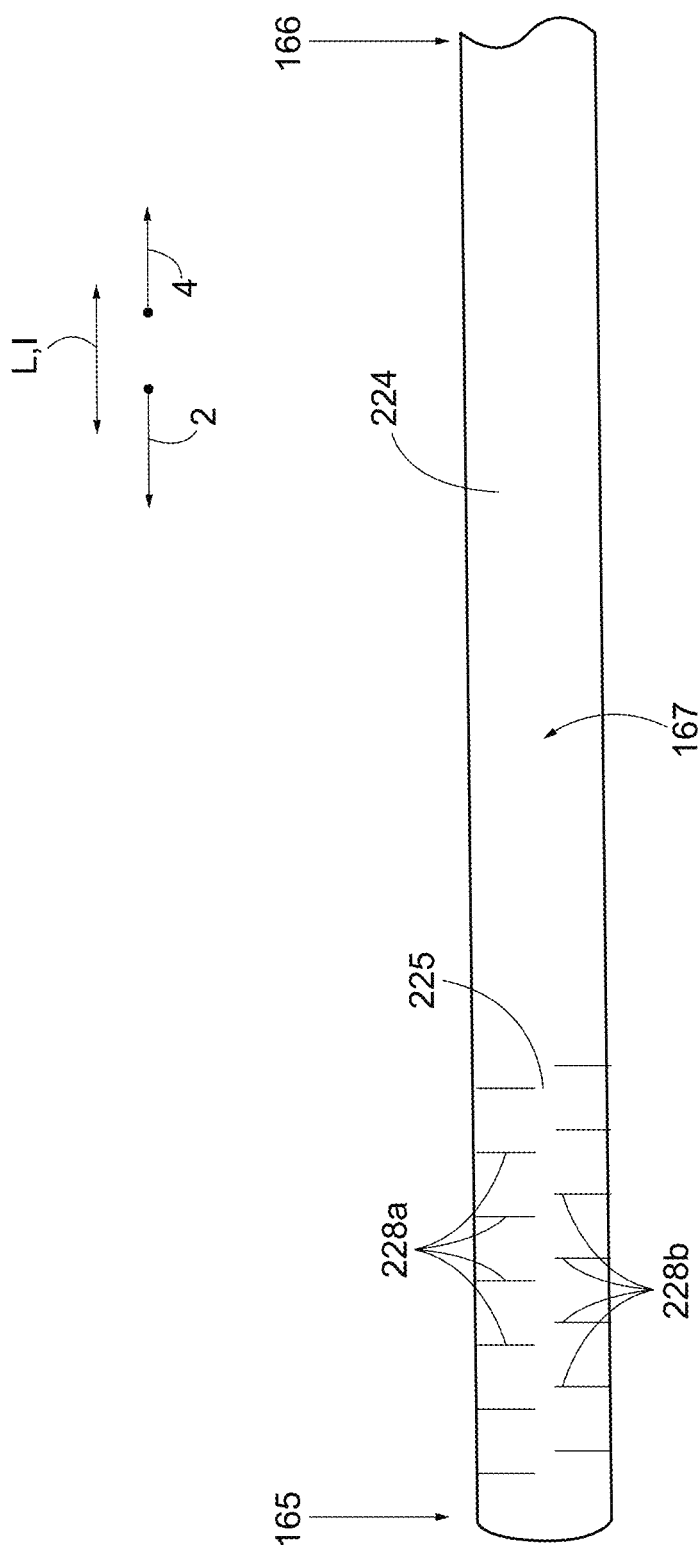
FIG. 7B is a top view of a distal portion of the tamper shown in FIG. 7A.
Figure 7C:
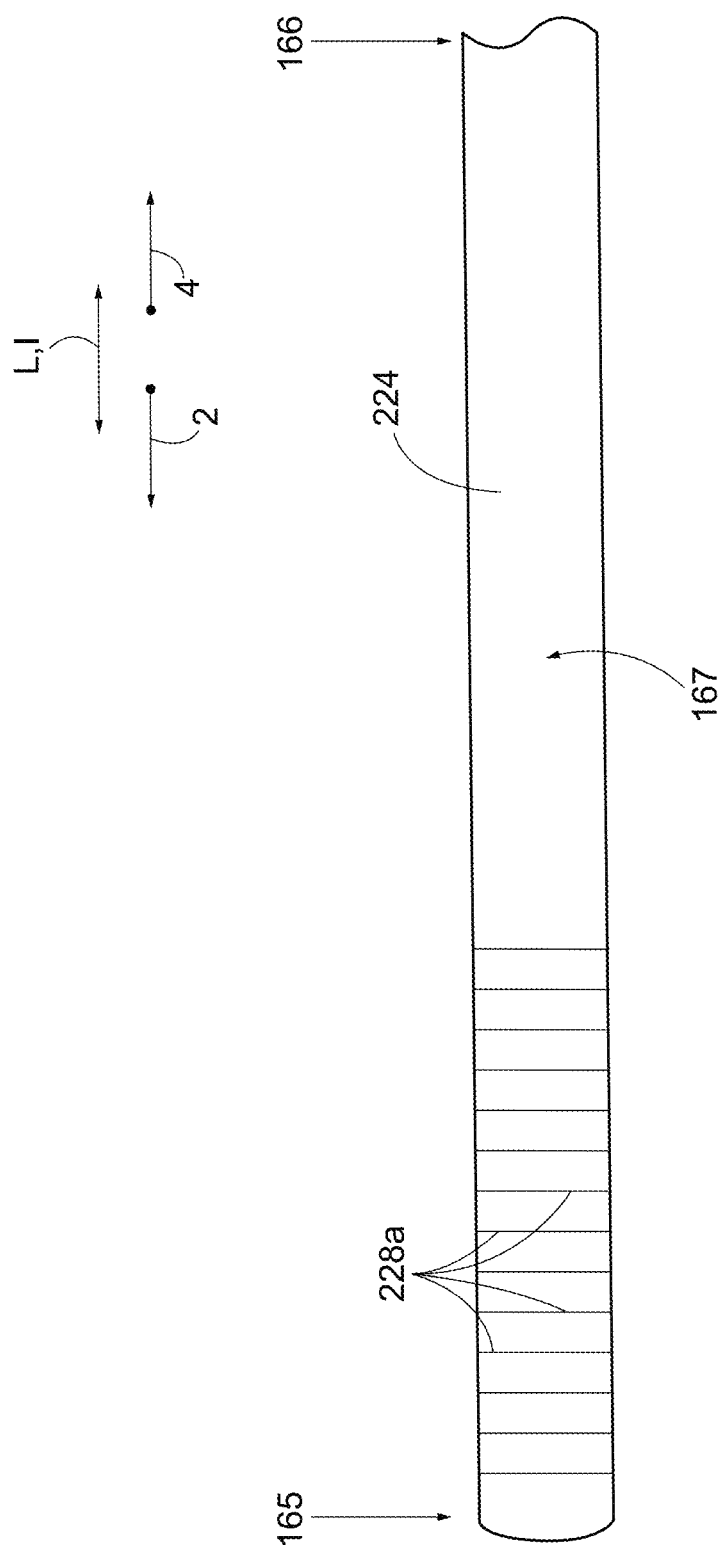
FIG. 7C is a side view of a distal portion of the tamper shown in FIG. 7A in an unflexed position.
Figure 7D:
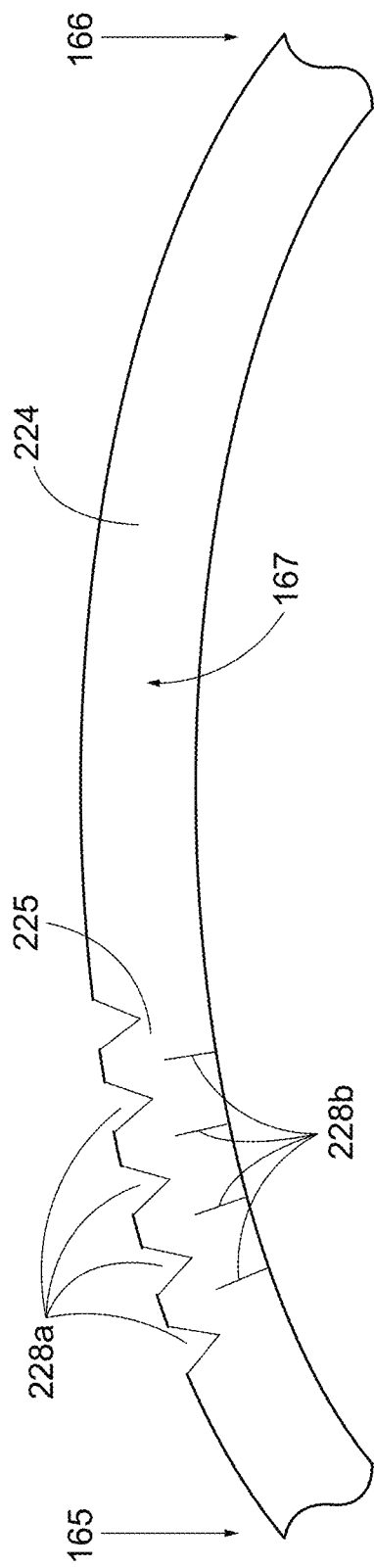
FIG. 7D is a side view of a distal portion of the tamper shown in FIG. 7C in a flexed position.

Continuing with FIGS. 7A-7D, the tamper tube 164 is configured to flex in a predetermined direction in order to aid remote tamping. The tamper 164 may include multiple cuts 228 that extend into the tamper tube body 224 toward a central axis (not shown) thereof to improve flexibility. More specifically, the tamper 164 may include at least one first cut 228a and at least one second cut 228b disposed opposite to the at least one first cut 228a. Alternatively, the tamper 164 may include a set of first cuts 228a and a set of second cuts 228b as shown in the figures. The set of first cuts 228a are offset with the respect to the set of second cuts 228b along the longitudinal direction L such that their respective cuts are not aligned along a common plane. Further, each set of cuts only extend partly into the tamper tube body 224 so that a zone of separation 225 is formed between them, on either side of the tamper 164. In this regard, the tamper 164 tends to flex along a first plane that extends through each set of cuts 228a and 228b. This is as opposed to flexing along a second plane that is perpendicular to and intersects the first plane or flexing along multiple planes or axes with a tamper that does not have such cuts formed therein. As shown in FIG. 7D, as the tamper flexes along a plane, the set of first cuts 228a open up while the set of second cuts compress. In the illustrated embodiment, the cuts 228a and 228b are straight slits extending partially into and around the tube body 224. In alternate embodiments, the cuts may be a single spiral cut that extend along a portion of the tube body. In such an embodiment, the tamper end may readily flex in multiple directions.

Referring to FIGS. 5A-6C, the tamper 164 includes a hub 232 and at least one track 240. The track 240, which may be referred to as a tamper track 240, has a distal end 233 coupled to the hub 232, a proximal end 234 opposite the distal end 233, and a series of gear teeth 242. The gear teeth 242 are configured to intermesh with the first gear 192 and the second gear 193 of the actuator 160. Thus, the actuator 160 is operably coupled to the tamper 164 via engagement of the track 240 with the gear assembly 174 of the actuator 160. In use, the gear assembly 174 transfers motion of the actuator 160 to the tamper 164. As a result, actuation of the actuator 160 causes the first gear 192 and the second gear 193 to rotate, causing the track 240, and thus the tamper 164 to translate along the longitudinal direction L. In the illustrated embodiment, the rotation of the actuator 160 causes the tamper 164 to translate in a distal direction 2 or proximal direction 4, depending on the direction of rotation of the actuator 160. More specifically, actuation of the actuator 160 in a second direction causes the tamper 164 to translate in a distal direction 2, and subsequent actuation of the actuator 160 in the first direction causes the tamper 164 to translate in the proximal direction 4 to release the suture assembly 152 from the sealing element 136, as explained further below.

Figure 8A:
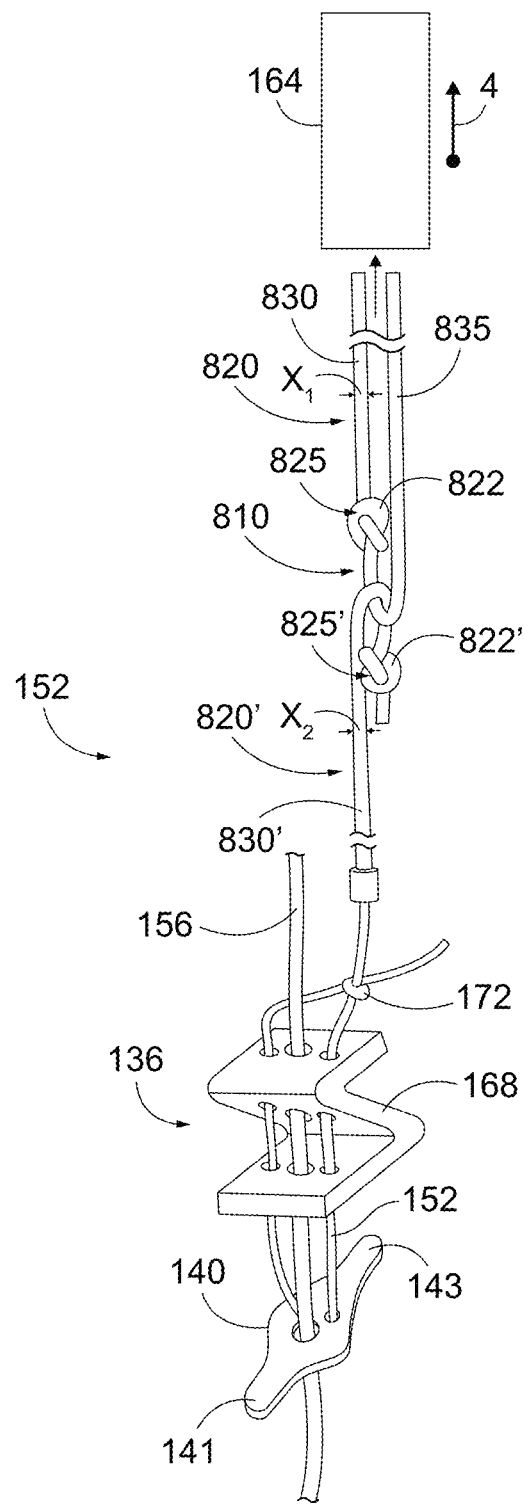
FIG. 8A is a schematic showing a releasable splice in a suture assembly disposed within the tamper, according to an embodiment of the present disclosure.

Referring to FIG. 8A, a suture assembly 152 coupled to the sealing element 136 is illustrated. As shown, the tamper 164 and suture assembly 152 are configured to facilitate release of the suture assembly 152 from the sealing element 136.

The suture assembly 152 may include a releasable splice or joint 810 contained with the tamper 164 prior to use. The releasable joint 810 is configured to release the suture assembly 152 from sealing element 136. The suture assembly 152 may include a first elongated element 820 and a second elongated element 820' that are overlaid over one another and reside within the tamper 164. The first elongated element 820 and the second elongated element 820' has a first coupling member 825 and a second coupling member 825', respectively. The first and second coupling members 825, 825' are intertwined with each other inside the tamper tube channel 227 of the tamper 164. The internal dimension of the tamper tube channel 227 is sized to allow a passage of a single coupling member, but with insufficient clearance to allow the two coupling members 285, 825' to pass one another within the tamper tube channel 227.

The tamper 164 together with the intertwined suture elongated elements 20, 20' form the splice or releasable joint 810. The releasable joint 810 is where the two elongated elements 20, 20' are joined within the tamper 164 and will support tension along the joined length. The releasable joint 810 is configured so as to withstand applied tensile forces to the lengths of material due to the tight fit of the coupling members 825, 825' within the opening of the tamper 164. Each respective coupling member 825, 825' is prevented from traversing the opposing loop with the other coupling member 825, 825' present in the channel 227. Thus, under a tensile load the joint 810 'jams' in the tamper 164 and acts as a useful splice.

Figure 8B:
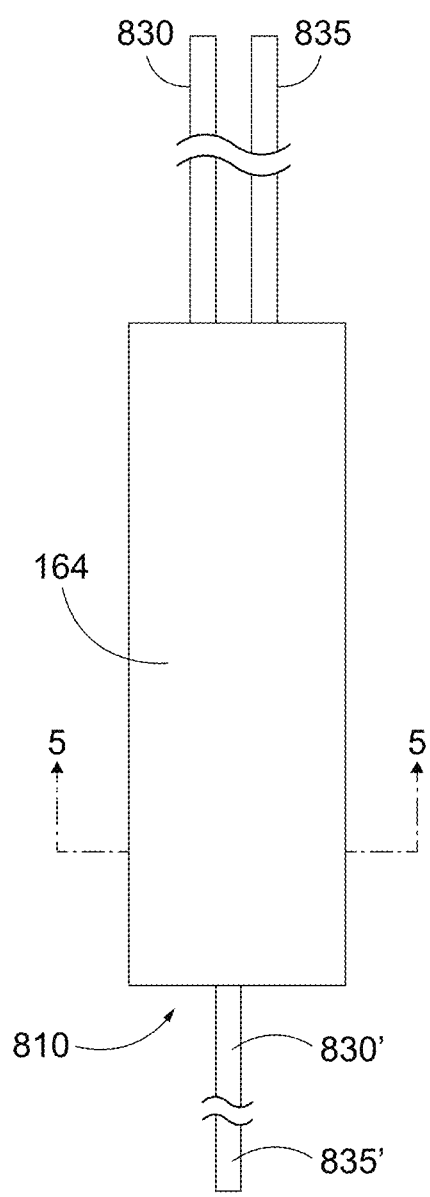
FIG. 8B depicts the releasable assembly shown in FIG. 1, illustrating the tamper positioned around the intertwined coupling ends of the elongated elements.
Figure 8C:
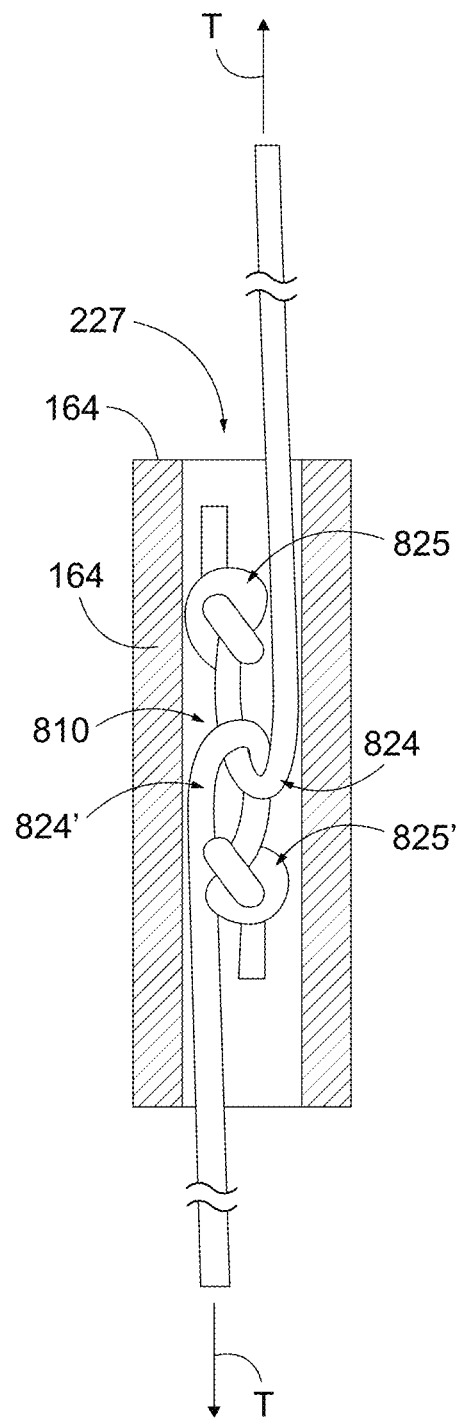
FIG. 8C is a partial sectional view of the releasable elongated assembly shown in FIG. 8B, illustrating how the elongated elements are captured within the tamper.

In operation, movement of the tamper 164 from a first position over the location of the entwinement of the two coupling members 825, 825' as shown in FIG. 8C, into a second position away from the entwinement, as shown in FIG. 8D, allows the two coupling members 825, 825' to be released from the tamper 164 and the two elongated elements 820, 820' to be released from one another. The first position of the tamper 164 shown in FIG. 8C may be referred to as the holding position. The second position of the release member as shown in FIG. 8D may be referred to as the releasing position. Furthermore, the first position may also be considered a first attached configuration where the tamper 164 captures the first coupling member 825, the releasable joint 810, and the second coupling member 825' so as to prevent release of the first and second elongated elements 20, 20' from each other. The second position may also be referred to as the second released configuration where the tamper 164 is moved along the longitudinal direction to release the first and second elongated elements 820, 820' from each other.

Continuing with FIGS. 8A-8E, the first and second elongated elements 820 and 820' each include first and second coupling members 825 and 825', respectively. The first elongated element 820 comprises has a first terminal end 835 with a coupling member 825 disposed proximate the first terminal end 835. Likewise, the second elongated element 820' includes a terminal end 835' and the other end is coupled to the sealing element 136 as shown in FIG. 8A. As illustrated, the second elongate element 820' has a second terminal end 835' with a second coupling member 825' proximate the second terminal end 835'. The length of material beyond coupling member 825 is utilized together with terminal end 835 to thread the joint 810 through the tamper 164 for the purpose of placing the tamper 164 over the joint 810, as shown in FIG. 8B.

The elongated elements 20, 20' may be any elongated length of material that form part of the suture assembly. The coupling members 825, 825' are designed to entrap each other within the tamper 164. The first coupling member 825 includes a first body 822 attached to (or monolithic with) the first elongated element 820 and the second coupling member 825' is a second body 822' attached (or monolithic with) the second elongated element 820'. As best shown in FIG. 8A and FIG. 8E, the first coupling member 825 defines a maximum cross-sectional dimension C1 that is greater than a cross-sectional dimension X1 of the first elongated element 820. Likewise, the second coupling member 825' defines a maximum cross-sectional dimension C2 that is greater than a cross-sectional dimension X2 of the second elongated element 820'. The cross-sectional dimension X1 and X2 are perpendicular to a central axis (not shown) of each respective elongated element. Furthermore, the combined maximum cross-sectional dimensions C1 and C2 is less than the dimension D of the tamper tube channel 227 of the tamper 164. This allows the two coupling members 825, 825' to be entrapped in the tamper 164, inhibiting each from passing by the other.

In accordance with the illustrated embodiment, the coupling members 825, 825' can be knots. For example, the first coupling member 825 is a first knot and the second coupling member 825' is a second knot. In such an example, the first and second knots are monolithic with the respect to the first and second elongated elements 820 and 820', respectively. In another alternative example, the first and second knots are separate from and attached to the first and second elongated elements 820 and 820', respectively. However, the coupling members can be any structure or device or structures having a variety of shapes that is generally larger than the cross-sectional dimension of the elongated elements 820, 820'.

In use, as the tamper 164 is advanced in a proximal direction 4 via operation of the actuator 160, the coupling members 825, 825' are released, thereby releasing a first portion 820 of the suture assembly 152 from the second portion 820' of the suture assembly 152. This in turn, releases the sealing element 136 from the deployment assembly 104. A suture tale, or second suture portion 820' will remain extending from the deployed sealing element 136 once the splice is released. The releasable joint 10 described above is similar to that described in WO 2017/192971 to Walters et al., the contents of which are incorporated herein by reference.

As shown, the deployment assembly 108 includes a single actuator 160 that causes the closure device 104 to transition through three actuation phases. In alternative embodiments, multiple actuators may be used. In such an embodiment the deployment assembly 108 can include a first actuator to release the toggle 140 and a second actuator that both advances the tamper 164 to tamp the sealing element 136 or retracts the tamper 164 to release the suture assembly 152. However, other types of actuators configured to transition the device through three actuation phases of release, tamp and suture release. In one example, the release component 144 and the tamper hub 232 may instead be structured as a series of fixed shafts that are connected at various points of rotation forming a parallelogram. An internal brace is coupled to the shafts the actuator. Actuation of the actuator 160 in this configuration would translate the points of rotation of the connected shafts such that rotation of the actuator 160 in a first direction would change the shape of the parallelogram to extend along the distal direction 2, while rotation of the actuator in a second direction would change the shape of the parallelogram to extend along the proximal direction 4, thereby causing retraction of the release component 144 and extension in the distal direction of the tamper 164. In yet another alternative embodiment, the actuator 160 may be a series of linear slides, such as a first (release) slide that is coupled to the release component 144 and a second (tamper) slide that is couple to the tamper 164. Tabs extend from each respective slide through the handle and can travel along respective guide tracks to allow the tabs to slide along the distal and proximal directions 2, 4. Thus, a user may retract a release slide to release the sealing element and translate a tamper slide to cause movement of the tamper 164. The tabs may extend from the handle along a transverse direction that is perpendicular to the longitudinal direction. Alternatively, the slides and tabs may extend in the proximal direction from the rear end 109 of the deployment assembly 108 such that pulling of tabs or pushing of the tabs cause the release component 144 and tamper 164 to move as described herein.

In accordance with the illustrated embodiment, the actuator 160 may be actuated in three phases. In the first phase, the actuator 160 is configured to rotate about the axis AP in a first direction. As the actuator 160 rotates in the first direction, the drive member 204 rotates in a first direction, thereby causing the gear assembly 174 to rotate in the first direction. Rotation of the gear assembly 174 in the first direction causes the tamper track 240 to translate along the longitudinal direction L in the proximal direction 4. Rotation of the gear assembly 174 in the first direction further causes the release track 185 to translate along the longitudinal direction L in the distal direction 2. Translation of the release track 185 causes the release component 144 to translate along the longitudinal direction L in the proximal direction 4 from a first or initial configuration relative to the delivery component 148 into a second or released configuration relative to the delivery component 148. In the released configuration, the sealing element 136 may be released from the release component 144, while still attached to the suture assembly 152. Specifically, the release component 144 releases the proximal end 143 of the toggle 140 from between the release component 144 and the delivery component 148. As the release component 144 moves in the proximal direction 4, the suture assembly 152 is pulled in the proximal direction 4 to thereby place the suture assembly 152 in tension. This causes a tensile force to be applied to the sealing element 136 The applied tensile force to the sealing element 136 releases the toggle 140. The applied tensile force urges the toggle 140 against the delivery component 148 and orients the toggle 140 into a position to seal the arterial wall.

In the second phase, the actuator 160 is configured to rotate about the axis AP in a second direction opposite the first direction. As the actuator 160 rotates in the first direction, the drive member 204 rotates in the first direction, thereby causing the gear assembly 174 to rotate in the second direction. Rotation of the gear assembly 174 in the second direction causes the release track 185 to translate along the longitudinal direction L in the proximal direction 4. Rotation of the gear assembly 174 in the first direction further causes the tamper track 240 to translate along the longitudinal direction L in the distal direction 2. Translation of the tamper track 240 causes the tamper 164 to translate along the longitudinal direction L in the distal direction 2 toward the sealing element 136. The tamper 164 tamps the sealing element 136 into a deployed configuration in the puncture of the arterial wall.

In the third phase, the actuator 160 is configured to rotate in the first direction. As the actuator 160 rotates in the first direction, the drive member 204 rotates in the first direction, thereby causing the gear assembly 174 to rotate in the first direction. Rotation of the gear assembly 174 in the first direction causes the tamper track 240 to translate along the longitudinal direction L in the proximal direction 4. Translation of the tamper track 240 causes the tamper 164 to translate along the longitudinal direction L in the proximal direction 4. As the tamper 164 is advanced in a proximal direction 4, the coupling members 825, 825' are released from the tamper 164, thereby releasing the first portion 820 of the suture assembly 152 from the second portion 820' of the suture assembly 152. This in turn, releases the sealing element 136 from the deployment assembly 108.

In an alternative embodiments, the actuator 160 may be actuated in two phases. In one example, in the first phase, the actuator 160 is configured to rotate in the first direction. As the actuator 160 rotates, the deployment assembly 108 releases the sealing element 136 therefrom while remaining coupled to the suture assembly 152. In the second phase, the actuator 160 is configured to rotate in a second direction opposite the first direction. As the actuator 160 rotates in the second direction, the tamper 164 translates in the longitudinal direction L in the distal direction 2 toward contact with the sealing element 136. In another example, in the first phase, the actuator 160 is configured to rotate in the first direction. As the actuator 160 rotates, the deployment assembly 108 releases the sealing element 136 therefrom while remaining coupled to the suture assembly and causes the tamper 164 to move in the distal direction 2 toward contact with the sealing element 136. In the second phase, the actuator 160 is configured to rotate in a second direction opposite the first direction. As the actuator 160 rotates in the second direction, the tamper 164 moves in the proximal direction 4 and releases the suture assembly 152 from the sealing element 136.

Embodiments of the present technology will now be described with respect to exemplary large bore procedures that utilize the aortic closure system illustrated in FIGS. 9A-9F. In order to perform any of the related procedures, the user gains percutaneous access to, for example, the femoral artery, causing a puncture site in the artery. To gain percutaneous access to the artery, the Seldinger technique may be used. For example, a hollow bore needle is inserted into the vessel 904 through a procedure sheath PS (referred to as the first access sheath). A guidewire is then advanced through the hollow needle into the femoral artery a sufficient distance to allow removal of the needle without the guidewire pulling out of the vessel. Removing the needle leaves the guidewire in place, with a portion of the guidewire extending into the artery and proximal end PE of the procedure sheath PS extending out of the patient. The guidewire, extending from outside the patient into the femoral artery, provides for an entry guide for other medical devices including the access sheath 112, the dilator 908, and the closure device 104. Therefore, once the guidewire is positioned in the vessel of the patient, catheters, or introducers, of gradually increasing diameters, are advanced over the guidewire and through the puncture into the artery to further open the puncture site. Then, a procedure access sheath set (i.e. an dilator 908 inside a procedure sheath PS) is moved along the guidewire such that a distal end DE of the procedure sheath PS moves into the vessel through the puncture site. And once positioned, the dilator 908 can be removed such that the procedure sheath PS provides for sizable access to the vessel interior from outside the body. After the relevant procedure is completed, the puncture site in the artery created during percutaneous access of the artery may be closed. The aortic closure system may be used to seal the puncture site.

In some instances, however, access through the femoral artery as described above is not indicated due to condition of the vessel between the femoral artery and the aorta. In such cases, a trans-caval procedure can be used to access the aorta. As shown in FIG. 8A, the trans-caval procedure includes guiding a guidewire 156 through a first puncture 912 in a vessel 904 and further into and a portion of the inferior vena cava 916. The method includes creating a second puncture 920 in the portion of the inferior vena cava 916 and creating a third puncture 922 in a femoral artery 928 and a portion of the aorta. The punctures may be formed with a tip of the guidewire 156, such as by burning. Next, the distal end DE of the procedure sheath PS is guided along the guidewire 156 through the second and third punctures. When the procedure sheath PS is in place, a medical device, such as a catheter, is inserted through the procedure sheath PS. When the procedure is completed, the catheter is removed from the procedure sheath PS and the guidewire 156.

Figure 9A:
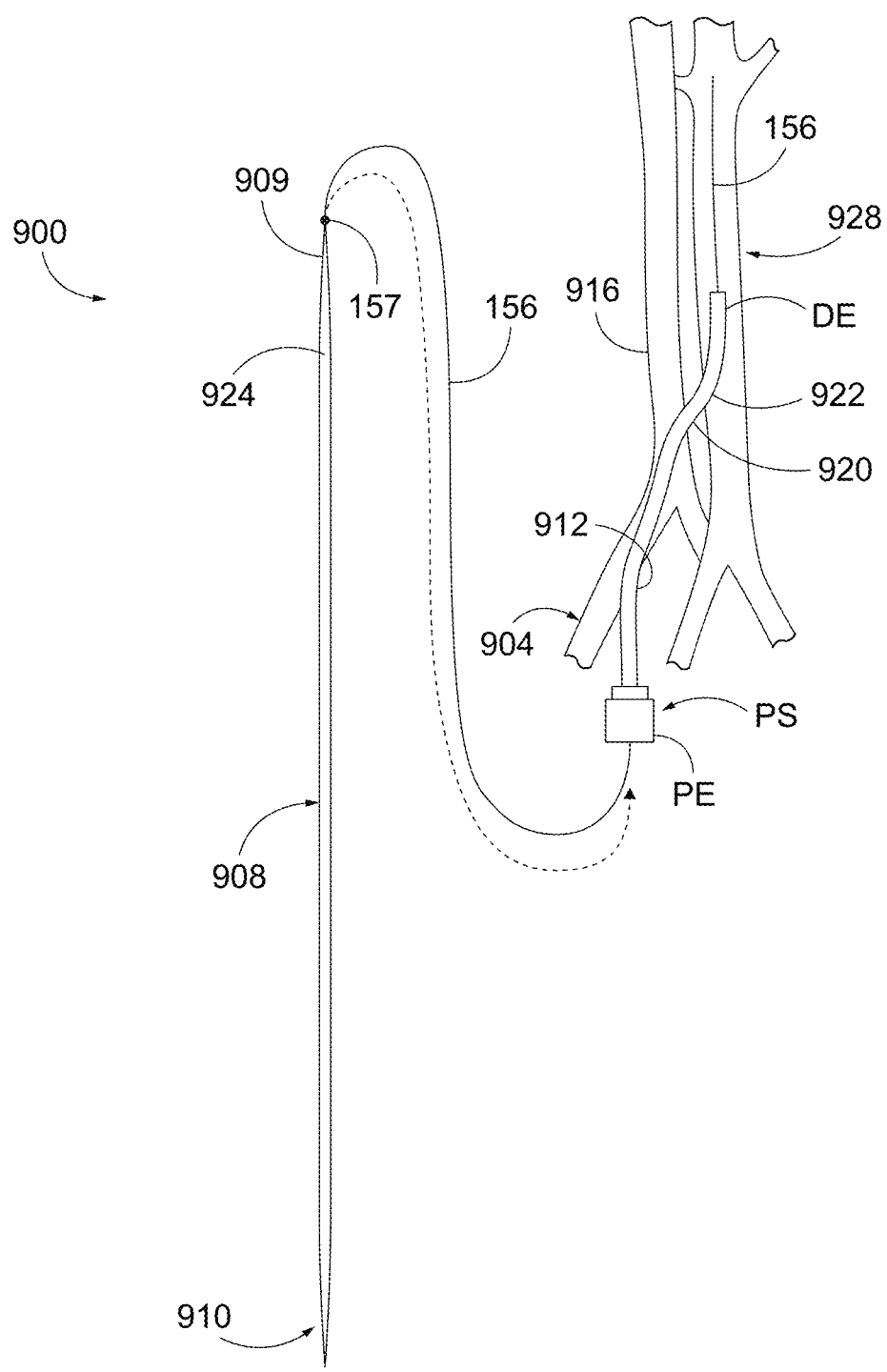
FIG. 9A is a schematic showing an access sheath from a cardiovascular surgical procedure partially disposed within a vessel through puncture sites in a vessel.

Continuing with FIG. 9A, the method includes positioning a tapered distal end 909 of a dilator 908 over a proximal end 157 of a guidewire 156 that extends through a puncture 912 in a vessel 904, e.g. a vena cava, such that the guidewire 156 enters a bore 910 of the dilator 908. In the example illustrated, the procedure sheath PS and guidewire 156 extends from outside the patient into the femoral venal cava.

Figure 9B:
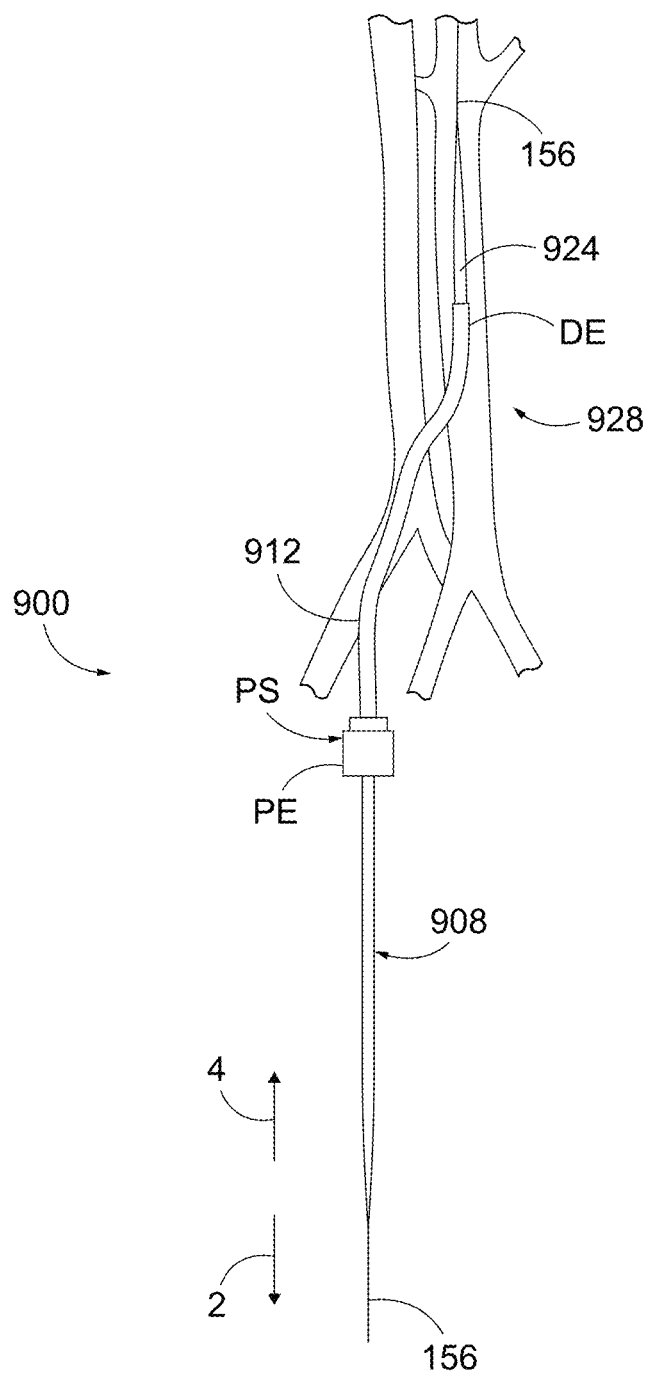
FIG. 9B is a schematic showing the introducer from FIG. 1 inserted in the access sheath shown in FIG. 9A.

Next, as shown in FIG. 9B, the method includes advancing the dilator 908 along the guidewire 156 in a distal direction 2 so that the tapered distal end enters the proximal end PE of the procedure sheath PS. The dilator 908 is further advanced out of a distal end DE of the procedure sheath PS that is spaced from the proximal end PE of the procedure sheath PS in the distal direction 2.

Figure 9C:
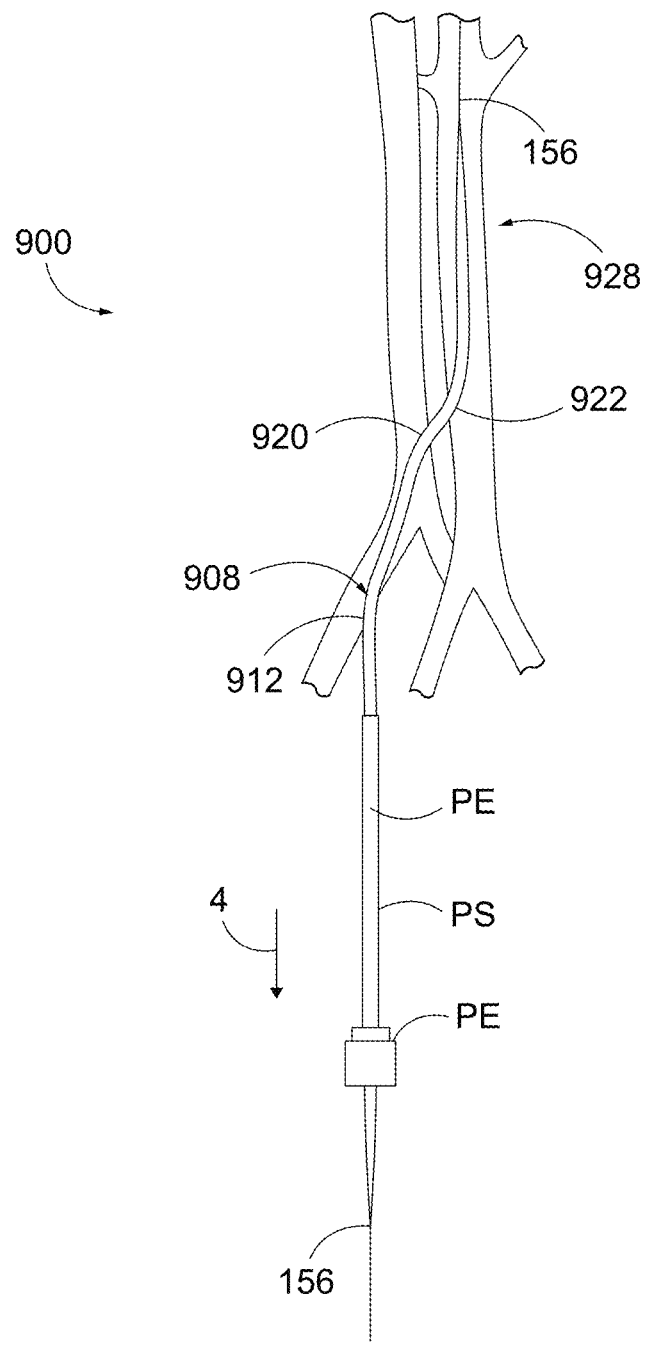
FIG. 9C is a schematic showing the removal of the access sheath from the vessel with the introducer remaining in position.

As shown in FIGS. 9B and 9C, the method includes removing the procedure sheath PS from the punctures 912, 920 and 922 while maintaining a portion of the tapered distal end 909 of the dilator 908 in the artery 928 (or some other vessel as the case may be).

Figure 9D:
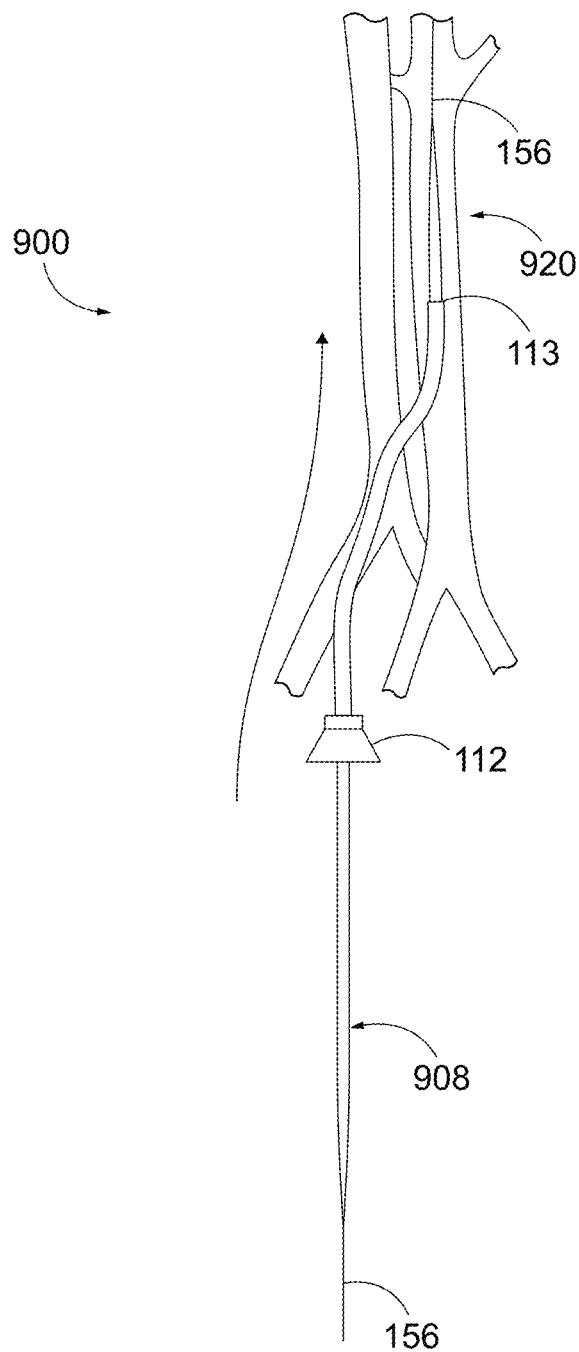
FIG. 9D is a schematic showing the access sheath of the system shown in FIG. 9A inserted into the vessel along the introducer sheath.

As shown in FIG. 9D, after the removing step, the procedure includes the step of inserting the access sheath 112 of system 900 over the tapered proximal end of the dilator 908 until the front end 128 of the access sheath 112 extends through the puncture of the vessel.

As shown in FIG. 9D, the method includes the step of removing the dilator 908 from the access sheath 112 and the guidewire 156. The exchange of sheaths PS and 112 limits blood loss and ensure smooth transition between the interventional procedure and sealing the puncture site.

Figure 9E:
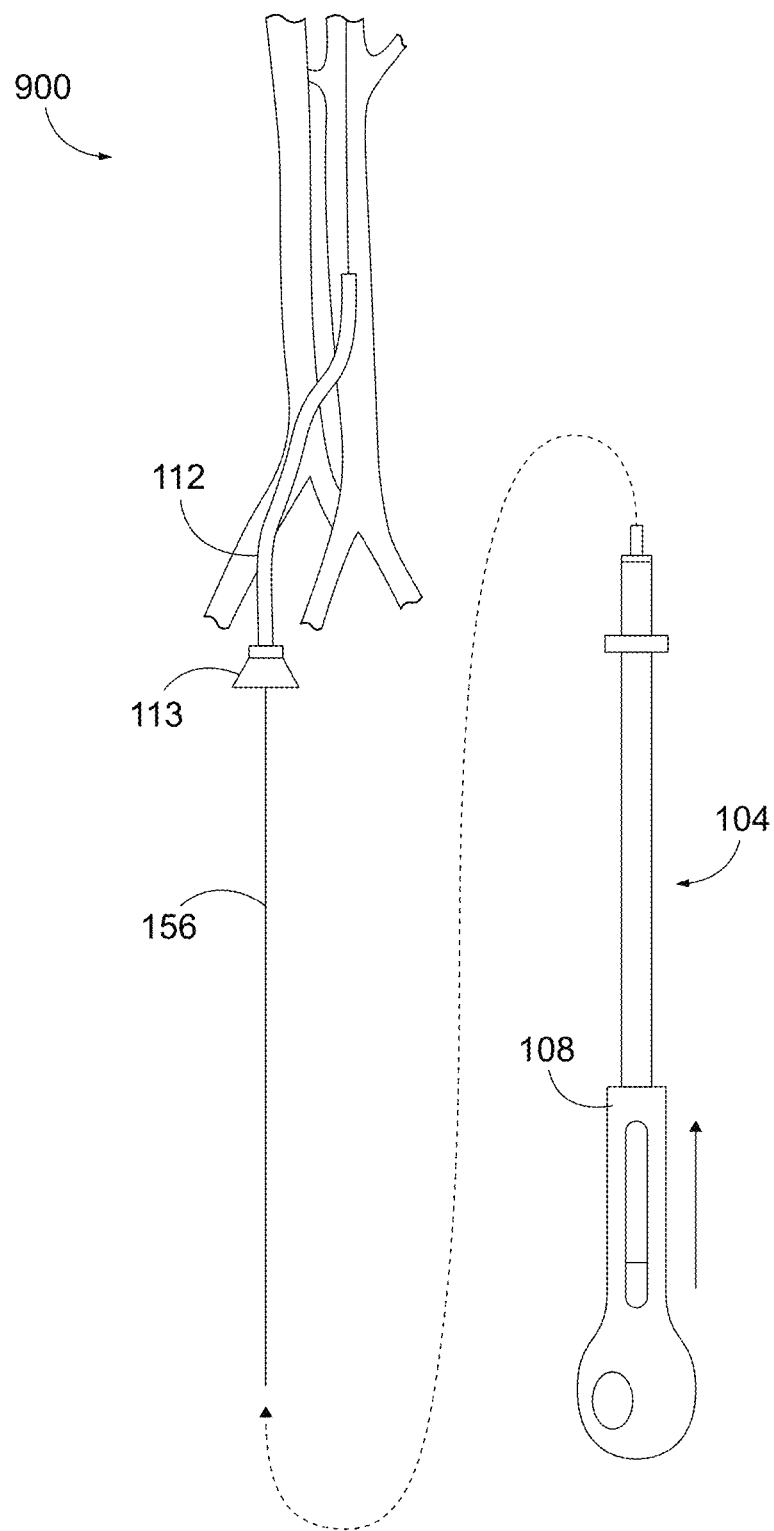
FIG. 9E is a schematic showing the introducer removed from the access sheath and the closure device positioned for insertion into the access sheath.
Figure 9F:
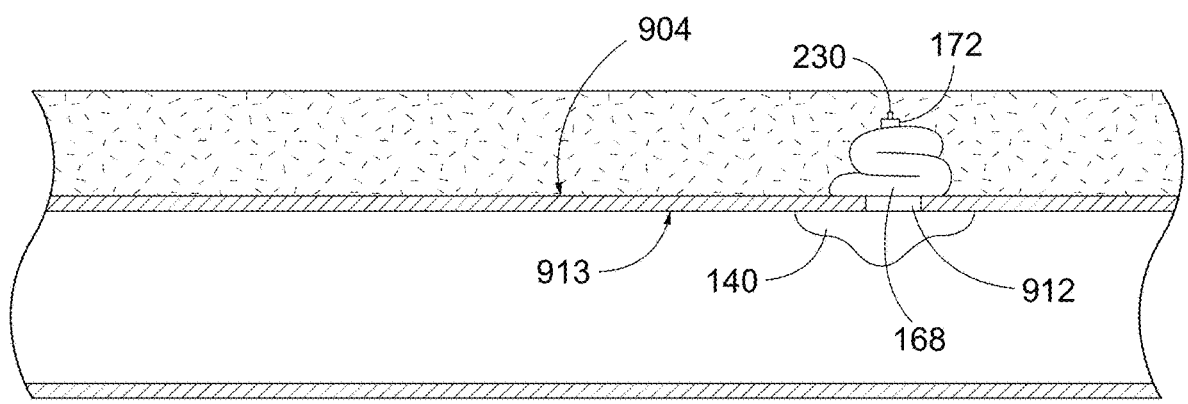
FIG. 9F is a schematic showing the sealing element fully sealing the puncture site.

As shown in FIG. 9E, the method includes advancing the closure device, for instance the deployment assembly 108, into the access sheath 112 to seal the puncture. Once the deployment assembly 108 is advanced, the actuator 160 is rotated in the first direction. The deployment assembly 108 releases the sealing element 136 while remaining coupled to the suture assembly 152. The actuator 160 is then rotated in the second direction, which causes the tamper 164 to move in a distal direction toward contact with the sealing element 136, such that the toggle 140 and plug 168 of the sealing element 136 are deployed into a sealing position against the puncture 912, as illustrated in FIG. 9F. As deployed, the toggle 140 is adjacent to the arterial wall 913, the plug 168 is collapsed against the outer surface of the wall 913 and opposite the toggle 140. The knot 172 and lock member 230 secure the plug 88 in place, compressing the plug 168 and toggle 140 together. The actuator 160 is then rotated in the first direction, which causes the tamper 164 to move in a proximal direction that is opposite the distal direction to release the suture assembly 152 from the sealing element 136. In one example, the method can also include the steps of sealing the puncture 922, sealing puncture 920 . . .

Figure 10:
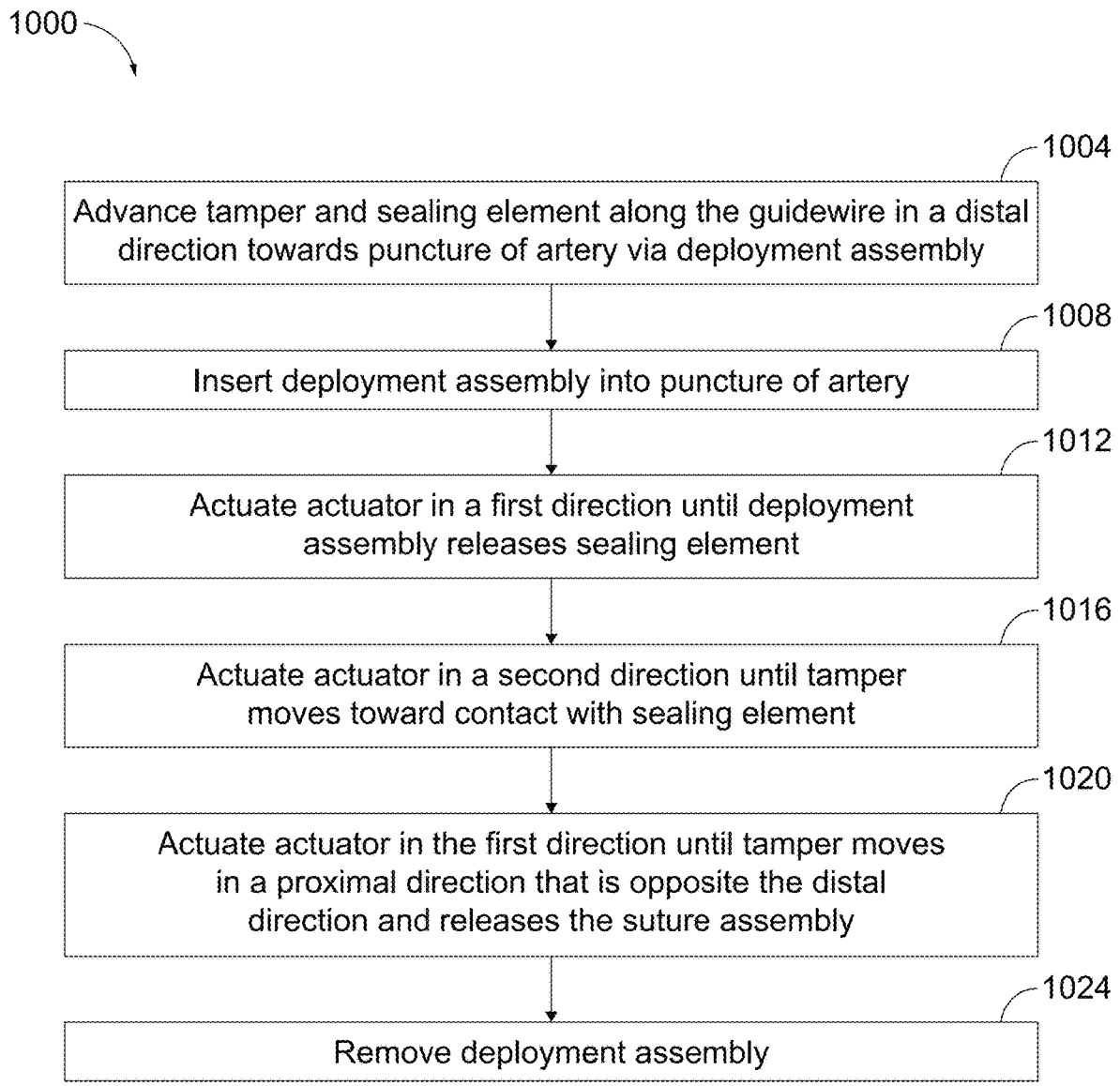
FIG. 10 is a process flow diagram illustrating a method for sealing an artery.

Now referring to FIG. 10, a method 1000 for closing a patient's artery with respect to large bore procedures that utilize the aortic closure system 100 shown in FIGS. 1-9F will be described. In step 1004, the tamper 164 and the sealing element 136 is advanced along the guidewire 156 in the distal direction 2 via the deployment assembly 108 towards a puncture of an artery. In step 1008, the deployment assembly is inserted into the puncture. In step 1012, during a first phase, the actuator 160 is actuated in a first direction until the deployment assembly 108 releases the sealing element 136. In step 1016, during a second phase, the actuator 160 is actuated in a second direction until the tamper 164 moves toward contact with the sealing element 136. The sealing element 136 is oriented in a sealing position in the artery. In step 1020, during a third phase, the actuator 160 is actuated in the first direction until the tamper 164 moves in the proximal direction 4 and releases the suture assembly 152.

The present disclosure include the following embodiments. However, the disclosure is not limited to the specific embodiment described below. Further certain features of the embodiments below may be interchangeable, such that features from one embodiment may be combined with features of one or more other embodiments.

A first embodiment of an aortic closure device includes a deployment assembly configured to be inserted in a puncture in an aorta, and a tamper carried by the deployment assembly. The tamper has a tamper channel that extends therethrough. The aortic closure devices includes a sealing element captured by the deployment assembly, and a suture assembly that extends through the tamper channel such that tamper is movable along the suture assembly. The suture assembly is releasably coupled to the sealing element. The aortic closure device includes an actuator coupled to the release tube, the delivery tube, and the tamper tube. In such an embodiment, the actuator has a) a first actuation phase that causes the deployment assembly to release the sealing element therefrom while remaining coupled to the suture assembly, b) a second actuation phase that causes the tamper to move in the distal direction toward contact with the sealing element, and c) a third actuation phase that causes the tamper to move in a proximal direction that is opposite the distal direction to release the suture assembly from the sealing element.

In the aortic closure device of embodiment 1, wherein the deployment assembly includes a release component that is elongate along a longitudinal direction, and a delivery component that is movable relative to the release component along the longitudinal direction, wherein the sealing element is captured by at least one of the release component and the delivery component. More specifically, the first actuation phase causes at least one of the release component and the delivery component to move in a distal direction that is aligned with the longitudinal direction to release the sealing element from the at least one of the release component and the delivery component.

In the aortic closure device of embodiment 1, wherein the suture assembly has a first portion releasably coupled to a second portion that is attached to the sealing element, wherein the third actuation phase causes the tamper to move in the proximal direction to release the sealing element from the first portion of suture assembly.

In the aortic closure device of embodiment 1, wherein the release tube has a release tube body that is elongate along the longitudinal direction. The release tube body defines a distal end, a proximal end, and a release tube channel that extends from the distal end of the release tube toward the proximal end of the release tube along the longitudinal direction.

In the aortic closure device of embodiment 1, wherein the delivery tube is disposed within the release tube channel, the delivery tube includes a delivery tube body, and a delivery tube channel that extends through the delivery tube body along the longitudinal direction.

In the aortic closure device of embodiment 1, wherein the tamper tube defines a distal end and a proximal end opposite the distal end along the longitudinal direction.

In the aortic closure device of embodiment 1, wherein movement of the tamper in the distal direction against the sealing element places the suture in tension and urges the sealing element against a distal end of the deployment assembly such that the sealing element is oriented in a sealing position.

In the aortic closure device of embodiment 1, further comprising a tensioner configured to control tension during actuation of the actuator. Furthermore, the tensioner includes a tensioner housing, a drag member configured to apply a frictional force to the suture assembly, and a spring coupled to the drag member and configured to maintain the suture assembly in tension after actuation of the actuator. In one example, the tensioner is positioned in a proximal direction relative to the release tube and receives the suture assembly such that the suture assembly passes through the tensioner housing, the drag member, and the spring.

In the aortic closure device of embodiment 1, wherein the actuator is rotatable about an actuator axis that is perpendicular to the longitudinal direction.

In the aortic closure device of embodiment 1, wherein the actuator further comprises a knob, a lever, or one or more linear slides.

In the aortic closure device of embodiment 1, the actuator further comprises a gear assembly that engages a first track of the release component and a second track of the tamper, wherein actuation of the actuator in the first direction causes first track to move and actuation of the actuator in the second direction cause the second track to move. In one example, the gear assembly includes a first gear and a second gear separated by a suture track, wherein the suture assembly extends along the suture track.

In the aortic closure device of embodiment 1, wherein actuation of the actuator in the first direction causes the release component to translate along the longitudinal direction and actuation of the actuator in the second direction causes the tamper to translate along the longitudinal direction.

In the aortic closure device of embodiment 1, wherein the distal end of the tamper includes at least a first cut and a second cut configured to permit the distal end of the tamper to flex.

In the aortic closure device of embodiment 1, wherein the suture assembly includes a releasable splice disposed in the tamper, wherein in the third actuation phase, the tamper retracts and causes the release of the releasable splice, thereby releasing the sealing element.

A second embodiment of an aortic closure device a deployment assembly configured to be inserted in a puncture in an aorta, and a tamper carried by the deployment assembly. The tamper has a tamper channel that extends therethrough. The aortic device includes a sealing element captured by the deployment assembly. The aortic closure device also includes a suture assembly that extends through the tamper channel such that tamper is movable along the suture assembly. The suture assembly is releasably coupled to the sealing element. The aortic closure device includes an actuator coupled to the release tube, the delivery tube, and the tamper tube. The actuator has a) a first actuation phase that causes the deployment assembly to release the sealing element therefrom while remaining coupled to the suture assembly, and b) a second actuation phase that causes the tamper to move in the distal direction toward contact with the sealing element.

In the aortic closure device of embodiment 2, wherein the deployment assembly includes a release component that is elongate along a longitudinal direction, and a delivery component that is movable relative to the release component along the longitudinal direction, wherein the sealing element is captured by at least one of the release component and the delivery component.

The first actuation phase of embodiment 2 causes at least one of the release component and the delivery component to move in a distal direction that is aligned with the longitudinal direction to release the sealing element from the at least one of the release component and the delivery component.

In the aortic closure device of embodiment 2, wherein movement of the tamper in the distal direction against the sealing element places the suture in tension and urges the sealing element against a distal end of the deployment assembly such that the sealing element is oriented in a sealing position.

In the aortic closure device of embodiment 2, further comprising a tensioner configured to control tension during actuation of the actuator.

In the aortic closure device of embodiment 2, wherein the actuator further comprises a knob, a lever, or one or more linear slides. Actuation of the actuator in the first direction causes the release component to translate along the longitudinal direction and actuation of the actuator in the second direction causes the tamper to translate along the longitudinal direction.

In the aortic closure device of embodiment 2, the distal end of the tamper includes at least a first cut and a second cut configured to permit the distal end of the tamper to flex.

A third embodiment of an aortic closure device includes a deployment assembly configured to be inserted in a puncture in an aorta, and a tamper carried by the deployment assembly. The tamper has a tamper channel that extends therethrough. The aortic device includes a sealing element captured by the deployment assembly. It also includes a suture assembly that extends through the tamper channel such that tamper is movable along the suture assembly. The suture assembly is releasably coupled to the sealing element. The aortic device includes an actuator coupled to the release tube, the delivery tube, and the tamper tube, the actuator has a) a first actuation phase that causes the deployment assembly to release the sealing element therefrom while remaining coupled to the suture assembly and causes the tamper to move in the distal direction toward contact with the sealing element, and b) a second actuation phase that causes the tamper to move in a proximal direction that is opposite the distal direction to release the suture assembly from the sealing element.

In the aortic closure device of embodiment 3, where the deployment assembly includes a release component that is elongate along a longitudinal direction, and a delivery component that is movable relative to the release component along the longitudinal direction. In such an embodiment the sealing element is captured by at least one of the release component and the delivery component.

In the aortic closure device of embodiment 3, the first actuation phase causes at least one of the release component and the delivery component to move in a distal direction that is aligned with the longitudinal direction to release the sealing element from the at least one of the release component and the delivery component.

In the aortic closure device of embodiment 3, the suture assembly has a first portion releasably coupled to a second portion that is attached to the sealing element. Furthermore, the third actuation phase causes the tamper to move in the proximal direction to release the sealing element from the first portion of suture assembly.

In the aortic closure device of embodiment 3, movement of the tamper in the distal direction against the sealing element places the suture in tension and urges the sealing element against a distal end of the deployment assembly such that the sealing element is oriented in a sealing position.

In the aortic closure device of embodiment 3, actuation of the actuator in the first direction causes the release component to translate along the longitudinal direction and actuation of the actuator in the second direction causes the tamper to translate along the longitudinal direction.

In the aortic closure device of embodiment 3, the distal end of the tamper includes at least a first cut and a second cut configured to permit the distal end of the tamper to flex.

In the aortic closure device of embodiment 3, the suture assembly includes a releasable splice disposed in the tamper, wherein in the third actuation phase, the tamper retracts and causes the release of the releasable splice, thereby releasing the sealing element.

A fourth embodiment of an aortic closure device includes a deployment assembly, a tamper carried by the deployment assembly, a sealing element carried by the deployment assembly, and a suture assembly releasably coupled to the sealing element. The aortic closure devices includes an actuator coupled to deployment assembly. The actuator has a) a first actuation phase that causes the deployment assembly to release the sealing element, b) a second actuation phase that causes the tamper to move in the distal direction along the suture assembly toward the sealing element, and c) a third actuation phase that causes the tamper to move in a proximal direction that is opposite the distal direction to release the sealing element from the suture assembly. The aortic closure device also includes a tensioner carried by the deployment assembly. The tensioner includes a drag member that is coupled to the suture assembly and configured to maintain the suture assembly in tension during actuation of the actuator.

In the aortic closure device of embodiment 4, movement of the tamper in the distal direction pulls the suture in the proximal direction, thereby placing the suture in tension and urging the sealing element against a distal end of the deployment assembly such that the toggle is oriented in the sealing position.

In the aortic closure device of embodiment 4, the tensioner further comprises a tensioner housing, and a spring coupled to the drag member and configured to maintain the suture assembly in tension after actuation of the actuator. In one example, the tensioner is positioned in a proximal direction relative to the release tube and receives the suture assembly such that the suture assembly passes through the tensioner housing, the drag member, and the spring.

A fifth embodiment of the present disclosure includes a tamper. The tamper includes a tamper body that is elongate along a longitudinal direction. The tamper body further defines a distal end, a proximal end opposite the distal end, and an outer surface. The tamper includes a tamper channel that extends from the proximal end to the distal end along the longitudinal direction. The tamper channel is configured to receive a suture assembly therethrough. Furthermore, at least one first cut at the distal end and that extends from the outer surface toward the tamper channel, and at least one second cut at the distal end opposite the first cut and that extends from the outer surface toward the tamper channel. In such an embodiment, the at least one first cut and the least one second cut are configured to permit the distal end of the tamper to flex.

In the tamper of embodiment 5, the at least one first cut and the at least one second cut are configured to permit the distal end to flex more readily along a first plane than a second plane that is perpendicular to and intersects the first plane. In one example, the at least one first cut and the at least one second cut extend only partially around the outer surface. In another example, the first cut is configured to open and the second cut is configured to compress when the tamper flexes along the plane.

In the tamper of embodiment 5, the first cuts and the second cut are separated by a portion of the outer surface.

In the tamper of embodiment 5, the at least one first cut is a set of first cuts, and the least one second cut is a set of second cuts, wherein the set of first cuts and the set of second cuts are offset with respect to each other along the longitudinal direction.

In the tamper of embodiment 5, the first cut and the second cut are slits.

In the tamper of embodiment 5, the first cut and the second cut are spiral cuts.

A sixth embodiment of an aortic closure device includes a release tube has a release tube body that is elongate along a longitudinal direction. The release tube defines a distal end, a proximal end, and a release tube channel that extends from the distal end of the release tube toward the proximal end of the release tube along the longitudinal direction. The aortic closure device also includes a delivery tube disposed within the release tube channel such that the delivery tube is movable relative to the release tube. The delivery tube includes a delivery tube body that defines a delivery tube channel that extends into the delivery tube body along the longitudinal direction. The aortic closure device includes a tamper tube disposed within the delivery tube channel such that the tamper tube is movable relative to the delivery tube. The tube defines a distal end, a proximal end, and a tamper tube channel. The aortic closure device includes a sealing element at least partially captured by the release tube, and a suture assembly that is attached to the sealing element and extends through the tamper tube channel. The aortic closure device includes an actuator coupled to the release tube, the delivery tube, and the tamper tube, the actuator has a) a first actuation phase that causes at least one of the release tube and the delivery tube to move in a distal direction to release the sealing element, b) a second actuation phase where actuation of the actuator causes the tamper tube to move in the distal direction relative to the delivery tube and into contact with the sealing element, and c) a third actuation phase where the tamper tube moves in a proximal direction that is opposite the distal direction to release the sealing element from the suture assembly.

A seventh embodiment of the present disclosure is a method for sealing a puncture of an artery. The method includes advancing a tamper that extends through at least a portion of a sealing element along a guidewire in a distal direction toward the puncture. In such an embodiment, the sealing element is coupled to a suture assembly and a deployment assembly supports the tamper and releasably holds the sealing element. The method further includes inserting the deployment assembly through the puncture of the artery. The method includes, during a first phase, actuating an actuator of the deployment assembly in a first direction until the deployment assembly releases the sealing element therefrom while remaining coupled to the suture assembly. The method includes during a second phase, actuating the actuator in a second direction until the tamper moves in the distal direction toward contact with the sealing element. The method also includes, during a third phase, actuating the actuator in the first direction until the tamper moves in a proximal direction that is opposite the distal direction and releases the suture assembly from the sealing element.

The method of embodiment 7, wherein the actuating step of the first phase further comprises moving at least one of a release component and a delivery component of the deployment assembly in a distal direction to release the sealing element from the at least one of the release component and the delivery component.

The method of embodiment 7, wherein the actuating step of the second phase further comprises moving the tamper in the distal direction against the sealing element places the suture assembly in tension and urges the sealing element against a distal end of the deployment assembly such that the sealing element is oriented in a sealing position.

The method of embodiment 7, wherein the actuating step of the third phase further comprises retracting the tamper and releasing a releasable splice of the suture assembly, thereby releasing the sealing element.

The method of embodiment 7, which further includes guiding a procedure sheath along the guidewire and into the puncture, and advancing a dilator over the guidewire such that the dilator enters the procedure sheath. Such a method further includes removing the procedure sheath, and inserting an access sheath of the deployment assembly over the dilator until the access sheath extends through the puncture. The method includes removing the dilator.

Certain terminology is used in the following description for convenience only and is not limiting. The words "right", "left", "lower" and "upper" designate directions in the drawings to which reference is made. The words "proximally" and "distally" refer to directions toward and away from, respectively, the individual operating the system. The terminology includes the above-listed words, derivatives thereof and words of similar import.

The present disclosure is described herein using a limited number of embodiments, these specific embodiments are not intended to limit the scope of the disclosure as otherwise described and claimed herein. Modification and variations from the described embodiments exist. More specifically, the following examples are given as a specific illustration of embodiments of the claimed disclosure. It should be understood that the invention is not limited to the specific details set forth in the examples.

What is claimed:

1. An aortic closure device, comprising:
   a deployment assembly configured to be inserted in a puncture in an aorta;
   a tamper carried by the deployment assembly, the tamper having:
      a tamper channel that extends therethrough,
      an outer surface,
      at least one first cut at a distal end of the tamper and that extends from the outer surface toward the tamper channel, and
      at least one second cut at the distal end of the tamper opposite the first cut and that extends from the outer surface toward the tamper channel, wherein the at least one first cut and the least one second cut are configured to permit the distal end of the tamper to flex;
   a sealing element captured by the deployment assembly;
   a suture assembly that extends through the tamper channel such that the tamper is movable along the suture assembly, the suture assembly being releasably coupled to the sealing element; and
   an actuator coupled to the deployment assembly, the actuator having a) a first actuation phase that causes the deployment assembly to release the sealing element therefrom while remaining coupled to the suture assembly, b) a second actuation phase that causes the tamper to move in a distal direction toward contact with the sealing element, and c) a third actuation phase that causes the tamper to move in a proximal direction that is opposite the distal direction to release the suture assembly from the sealing element.

2. The aortic closure device of claim 1, wherein the deployment assembly includes a release component that is elongate along a longitudinal direction, and a delivery component that is movable relative to the release component along the longitudinal direction, wherein the sealing element is captured by at least one of the release component and the delivery component.

3. The aortic closure device of claim 2, wherein the first actuation phase causes at least one of the release component and the delivery component to move in a distal direction that is aligned with the longitudinal direction to release the sealing element from the at least one of the release component and the delivery component.

4. The aortic closure device of claim 2, the actuator further comprises a gear assembly that engages a first track of the release component and a second track of the tamper, wherein actuation of the actuator in a first direction causes the first track to move and actuation of the actuator in a second direction causes the second track to move.

5. The aortic closure device of claim 4, wherein the gear assembly includes a first gear and a second gear separated by a suture track, wherein the suture assembly extends along the suture track.

6. The aortic closure device of claim 2, wherein actuation of the actuator in the a direction causes the release component to translate along the longitudinal direction and actuation of the actuator in a second direction causes the tamper to translate along the longitudinal direction.

7. The aortic closure device of claim 1, wherein the suture assembly has a first portion releasably coupled to a second portion that is attached to the sealing element, wherein the third actuation phase causes the tamper to move in the proximal direction to release the sealing element from the first portion of suture assembly.

8. The aortic closure device of claim 1, further comprising a tensioner configured to control tension during actuation of the actuator.

9. The aortic closure device of claim 8, wherein the tensioner includes a tensioner housing, a drag member configured to apply a frictional force to the suture assembly, and a spring coupled to the drag member and configured to maintain the suture assembly in tension after actuation of the actuator.

10. The aortic closure device of claim 9, wherein the deployment assembly comprises a release tube, the tensioner is positioned in the proximal direction relative to the release tube and receives the suture assembly such that the suture assembly passes through the tensioner housing, the drag member, and the spring.

11. The aortic closure device of claim 1, wherein the actuator further comprises a knob, a lever, or one or more linear slides.

12. The aortic closure device of claim 1, wherein the deployment assembly comprises a release tube, the release tube has a release tube body that is elongate along the longitudinal direction, the release tube body defining a distal end, a proximal end, and a release tube channel that extends from the distal end of the release tube toward the proximal end of the release tube along the longitudinal direction.

13. The aortic closure device of claim 12, wherein the deployment assembly comprises a delivery tube, the delivery tube is disposed within the release tube channel, the delivery tube including a delivery tube body, and a delivery tube channel that extends through the delivery tube body along the longitudinal direction.

14. The aortic closure device of claim 1, wherein the deployment assembly comprises a tamper tube, the tamper tube defines a distal end and a proximal end opposite the distal end along the longitudinal direction.

15. The aortic closure device of claim 1, wherein movement of the tamper in the distal direction against the sealing element places the suture in tension and urges the sealing element against a distal end of the deployment assembly such that the sealing element is oriented in a sealing position.

16. The aortic closure device of claim 1, wherein the actuator is rotatable about an actuator axis that is perpendicular to the longitudinal direction.

17. The aortic closure device of claim 1, wherein the suture assembly includes a releasable splice disposed in the tamper, wherein in the third actuation phase, the tamper retracts and causes the release of the releasable splice, thereby releasing the sealing element.

* * * * *